(12) United States Patent
Nelson

(10) Patent No.: US 8,603,038 B2
(45) Date of Patent: Dec. 10, 2013

(54) BURR HOLE ANCHORS, SYSTEMS, AND METHODS

(75) Inventor: Brian D. Nelson, Birchwood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1292 days.

(21) Appl. No.: 12/357,120

(22) Filed: Jan. 21, 2009

(65) Prior Publication Data

US 2009/0187149 A1 Jul. 23, 2009

Related U.S. Application Data

(60) Provisional application No. 61/022,643, filed on Jan. 22, 2008.

(51) Int. Cl.
*A61M 5/32* (2006.01)

(52) U.S. Cl.
USPC .......................................................... 604/175

(58) Field of Classification Search
USPC .................................. 604/175, 288.01, 264
See application file for complete search history.

(56) References Cited

U.S. PATENT DOCUMENTS

| | | | |
|---|---|---|---|
| 3,760,811 A | 9/1973 | Andrew | |
| 4,328,813 A | 5/1982 | Ray | |
| 4,350,159 A | 9/1982 | Gouda | |
| 4,995,856 A | 2/1991 | Heindl et al. | |
| 5,464,446 A | 11/1995 | Dreesen et al. | |
| 5,713,858 A | 2/1998 | Heruth et al. | |
| 5,843,150 A | 12/1998 | Dreessen et al. | |
| 5,865,842 A * | 2/1999 | Knuth et al. | 607/116 |
| 5,916,200 A | 6/1999 | Eppley et al. | |
| 5,927,277 A | 7/1999 | Baudino et al. | |
| 5,954,687 A | 9/1999 | Baudino | |
| 6,044,304 A | 3/2000 | Baudino | |
| 6,134,477 A | 10/2000 | Knuteson | |
| 6,321,104 B1 | 11/2001 | Gielen et al. | |
| 6,356,792 B1 | 3/2002 | Errico et al. | |
| 6,482,182 B1 | 11/2002 | Carroll et al. | |
| 7,204,840 B2 | 4/2007 | Skakoon et al. | |
| 7,331,613 B2 | 2/2008 | Schulte | |
| 2003/0199831 A1 | 10/2003 | Morris et al. | |
| 2005/0054985 A1 | 3/2005 | Mogg | |

(Continued)

FOREIGN PATENT DOCUMENTS

| EP | 1426074 A1 | 6/2004 |
|---|---|---|
| EP | 1426074 | 11/2006 |

(Continued)

OTHER PUBLICATIONS

U.S. Appl. No. 12/276,794, filed Nov. 24, 2008, Nelson.

*Primary Examiner* — Kevin C Sirmons
*Assistant Examiner* — Brandy S Lee
(74) *Attorney, Agent, or Firm* — Mueting, Raasch & Gebhardt, P.A.

(57) ABSTRACT

Anchors for securing a therapy delivery device such as a therapy catheter relative to a burr hole, and systems and methods for using the same. Anchors in accordance with embodiments of the present disclosure may include various apparatus for securing the therapy catheter relative to the burr hole. Exemplary anchors may include one or more of a connector for selectively connecting the therapy catheter to an external therapy source, and a shearing mechanism for shearing the therapy catheter to the desired length.

27 Claims, 26 Drawing Sheets

(56) References Cited

U.S. PATENT DOCUMENTS

| | | | |
|---|---|---|---|
| 2005/0096633 A1* | 5/2005 | Moskowitz | 604/508 |
| 2005/0143800 A1 | 6/2005 | Lando et al. | |
| 2005/0182425 A1 | 8/2005 | Schulte et al. | |
| 2006/0111688 A1 | 5/2006 | Kraus et al. | |
| 2006/0129126 A1 | 6/2006 | Kaplitt et al. | |
| 2006/0135945 A1 | 6/2006 | Bankiewicz et al. | |
| 2008/0097287 A1 | 4/2008 | Nelson et al. | |
| 2008/0103456 A1* | 5/2008 | Johnson et al. | 604/264 |
| 2008/0172068 A1 | 7/2008 | Adams et al. | |
| 2009/0143764 A1 | 6/2009 | Nelson | |

FOREIGN PATENT DOCUMENTS

| | | |
|---|---|---|
| WO | WO 97/42870 | 11/1997 |
| WO | WO 98/08554 A1 | 3/1998 |
| WO | WO 03/068304 A1 | 8/2003 |
| WO | WO 2004/026161 A2 | 4/2004 |
| WO | WO 2004/026161 A3 | 7/2004 |
| WO | WO 2004/105640 A2 | 12/2004 |
| WO | WO 2004/105640 A3 | 12/2004 |

* cited by examiner

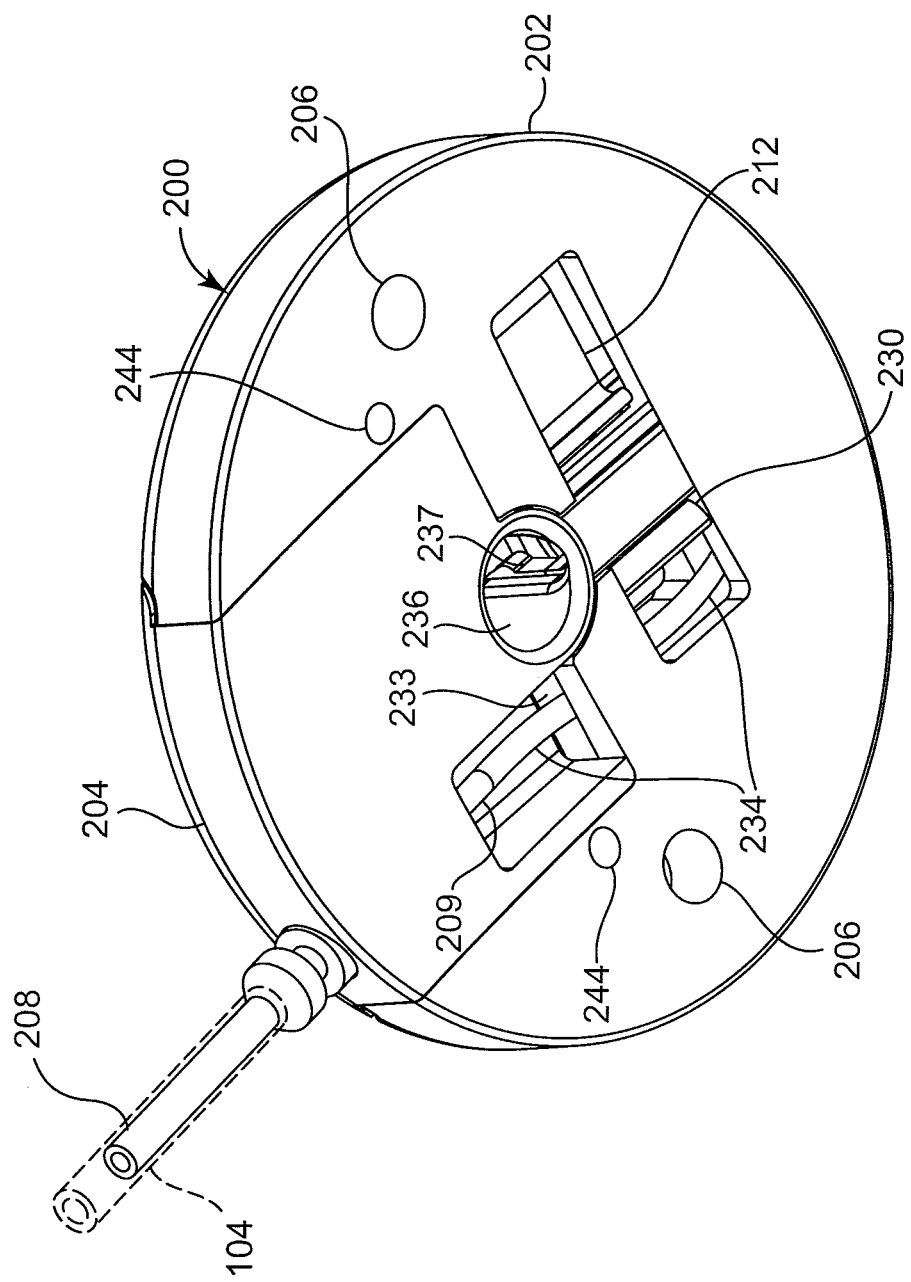

BURR HOLE ANCHORS, SYSTEMS, AND METHODS

This application claims the benefit of U.S. Provisional Application No. 61/022,643, filed 22 Jan. 2008, the content of which is incorporated herein by reference in its entirety.

TECHNICAL FIELD

The present invention relates generally to medical devices and, more particularly, to anchors for securing a therapy delivery device (e.g., a catheter) within or otherwise relative to a body portal such as a cranial burr hole, and to systems and methods incorporating the same.

BACKGROUND

Medical procedures involving access to the brain through a burr hole in the skull are used to treat a variety of medical conditions. For example, electrical stimulation of the brain to relieve chronic pain, or for the treatment of movement disorders, may necessitate access via a burr hole. Similarly, burr holes are typically formed to allow implantation of a catheter, e.g., an intraparenchymal (IPA) or intracerebroventricular catheter, to treat various ailments.

Use of a catheter to deliver a therapeutic agent to the brain generally involves the insertion of the catheter into the brain and dispensing the agent at the desired location. During a typical implantation procedure, an incision may be made in the scalp to expose the patient's skull. After forming a burr hole through the skull, the catheter may be inserted into the brain. To accurately place the catheter and avoid unintended injury to the brain, surgeons typically use stereotactic apparatus/procedures. One exemplary stereotactic apparatus is described in U.S. Pat. No. 4,350,159 to Gouda, which may be used to position, for example, an electrode.

As one can appreciate, once an inserted device such as a catheter is properly positioned, it is important that it be adequately immobilized to prevent movement of its distal, therapy delivering tip from its intended location. Even minimal movement of the device tip may reduce therapeutic efficiency. Accordingly, reliable methods and apparatus for anchoring and securing the device relative to the burr hole are desirable.

In typical implantations, a proximal end of the device (e.g., a therapy catheter) may extend out of the burr hole and be anchored at the burr hole with an anchoring device. The free end of the therapy catheter may then be tunneled beneath the skin and connected to a secondary delivery catheter that is, in turn, coupled to a source (e.g., an implanted infusion pump) containing the therapeutic agent. As a result, the agent may be delivered through the delivery catheter and the therapy catheter to the desired location within the patient. As one may appreciate, the two catheters may require accurate pre-sizing (prior to implantation) to ensure that their respective coupling ends are ultimately proximate one another prior to connection.

During and after implantation, various bodily forces may act on portions of the therapy catheter that extend outside of the burr hole. Depending on the anchor design, these forces could be sufficient to eventually shift the therapy catheter, and thus its distal end, away from the desired location. Even slight forces applied to the therapy catheter may result in shifting of its distal end. For example, bodily induced forces such as those resulting from patient movement, forces transferred through the scalp, or changes in the surrounding tissue (e.g., swelling), may result in movement of the therapy delivery catheter.

SUMMARY

Embodiments of the present invention may overcome these and other issues by isolating various bodily forces from the distal, implanted tip of the therapy catheter, thus reducing or preventing unintended tip movement resulting from such forces. Moreover, embodiments of the present invention may permit cutting or trimming of the therapy catheter during implantation, as well as apparatus/methods for staging and immobilizing the therapy catheter both during cutting and subsequent attachment of the therapy catheter to other components, e.g., to a feed catheter.

In one embodiment, a burr hole anchor for anchoring a therapy delivery device is provided, the anchor having a body including a base operable to secure to bone surrounding a burr hole. The body includes engagement surfaces configured to receive and immobilize a therapy catheter passing through the burr hole. The anchor further includes a connector operatively coupled to the base and movable relative thereto between at least: a coupled position, wherein the connector is fluidly connected to the therapy catheter, and an uncoupled position, wherein the connector is disconnected from the therapy catheter.

The anchor may optionally include other features. For instance, the anchor may further include a guide fixed relative to the base and proximate the engagement surfaces, wherein the guide comprises a trough configured to receive and support the connector for translation therein. Further, the connector of the anchor may be movable in a radial direction relative to the base. In another embodiment, the connector may include: a therapy catheter feed pin configured to engage the therapy catheter when the connector is in the coupled position; a supply pin operatively coupled to an infusion pump, the supply pin in fluid communication with the therapy catheter feed pin; and an actuator for moving the connector from the uncoupled position to the coupled position. The body may further include a delivery catheter feed pin and a supply conduit fluidly connecting the delivery catheter feed pin with the supply pin. The delivery catheter feed pin may, in one embodiment, be fixed to the base. In still another embodiment, the base of the body of the anchor may include a frame defining one or more bays, each bay configured to receive an anchor module. The anchor module may include a module selected from the group consisting of a blanking module, a catheter connection module, and a pressure measurement module. Moreover, the connector may be attached directly to the anchor module in some embodiments. In another embodiment, the connector is attached directly to the base. In still another embodiment, the body of the anchor may define an opening through which the therapy catheter may pass, and the engagement surfaces may be defined by a slot formed through a wall of the opening. The anchor may further include a catheter shearing mechanism attached to the body. The catheter shearing mechanism may include a door operatively attached to the body and pivotable between an open position and a closed position, the door including a shearing edge.

In another embodiment, a burr hole anchor for anchoring a therapy delivery device is provided. The anchor includes a body having a base operable to secure to bone surrounding a burr hole, wherein the body includes engagement surfaces configured to receive and immobilize a therapy catheter passing through the burr hole. The anchor further includes a shearing mechanism having a door operatively attached to the body, the door pivotable between an open position and a closed position, the shearing mechanism operable to selectively shear the therapy catheter when placed between a first shearing edge formed by the door and a second shearing edge formed by the body. In one embodiment, the anchor may optionally include a clip removably secured to the body and operable to hold an excess portion of the therapy catheter. The base of the anchor may optionally include a frame defining one or more bays, each bay configured to receive an anchor module, wherein the anchor module includes a module selected from the group consisting of a blanking module, a catheter connection module, and a pressure measurement module. In one embodiment, the second shearing edge of the shearing mechanism is defined by an edge of a slot formed in the body for receiving the door. The body may also define a depression adjacent the second shearing edge, the depression configured to receive the therapy catheter therein. In another embodiment, the body of the anchor further defines a channel adjacent the depression, the channel configured to receive the therapy catheter therein.

In yet another embodiment, a burr hole anchor system is provided that includes: a therapy catheter for placement through a burr hole; and a burr hole anchor. The burr hole anchor includes a body having a base operable to secure to bone surrounding the burr hole, wherein the base includes a frame defining one or more bays. The anchor further includes an anchor module securable in each of the one or more bays, wherein the anchor module includes a module selected from the group consisting of a blanking module, a catheter connection module, and a pressure measurement module. The catheter connection module may, in some embodiments, include a connector movable between at least: a coupled position, wherein the connector is fluidly connected to the therapy catheter; and an uncoupled position, wherein the connector is disconnected from the therapy catheter. The catheter connection module may, in some embodiments, further include a catheter shearing mechanism comprising a door forming a first shearing edge, the door pivotable between an open position and a closed position.

In still yet another embodiment, a burr hole anchor system is provided including: a therapy catheter for placement through a burr hole; and a burr hole anchor. The burr hole anchor includes a body having a base operable to secure to bone surrounding the burr hole, wherein the body includes engagement surfaces configured to receive and immobilize the therapy catheter passing through the burr hole. The anchor also includes a catheter shearing mechanism attached to the body, wherein the catheter shearing mechanism includes a door pivotally attached to the body and moveable between an open position and a closed position, the door having a first shearing edge and the body defining a second shearing edge. The anchor system may optionally include a connector operatively coupled to the base and movable relative thereto between at least: a coupled position, wherein the connector is fluidly connected to the therapy catheter; and an uncoupled position, wherein the connector is disconnected from the therapy catheter. The system may also optionally include an infusion pump and a delivery catheter, the delivery catheter including a first end fluidly coupled to the connector, and a second end fluidly coupled to the infusion pump.

In again yet another embodiment, a method for trimming a therapy catheter and for securing the therapy catheter relative to a burr hole is provided. The method includes: placing the therapy catheter through the burr hole; and securing the therapy catheter relative to bone surrounding the burr hole using a burr hole anchor. The anchor includes a body having a base that is securable to the bone surrounding the burr hole, wherein the body includes engagement surfaces configured to receive and immobilize the therapy catheter passing through the burr hole. The anchor also includes a shearing mechanism having a door pivotally attached to the body and pivotable between an open position and a closed position, the shearing mechanism including a first shearing edge and a second shearing edge. The method further includes: placing the therapy catheter between the first and second shearing edges; and moving the door from the open position to the closed position, thereby shearing an excess portion of the therapy catheter.

The above summary is not intended to describe each embodiment or every implementation of the present invention. Rather, a more complete understanding of the invention will become apparent and appreciated by reference to the following Detailed Description of Exemplary Embodiments in view of the accompanying figures of the drawing.

BRIEF DESCRIPTION OF THE VIEWS OF THE DRAWING

The present invention will be further described with reference to the figures of the drawing, wherein:

FIGS. 6A-6B illustrate bottom perspective views of the anchor of FIG. 2, wherein: FIG. 6A is a view of the whole anchor; and FIG. 6B is an exploded view of an insert or module of the anchor;

FIGS. 10A-10B illustrate a method of using the anchor of FIG. 7, wherein: FIG. 10A is a perspective view with a shearing mechanism, e.g., door, of the anchor shown in an open position and with a clip attached, the shearing mechanism shown prior to shearing the therapy catheter; FIG. 10B is a perspective view with the door shown in a closed position after shearing the catheter.

FIGS. 11A-11B are cross-sectional views of the anchor of FIG. 7, wherein: FIG. 11A shows the connector of the anchor in a first or uncoupled position; and FIG. 11B shows the connector in a second or coupled position;

Figure 1:
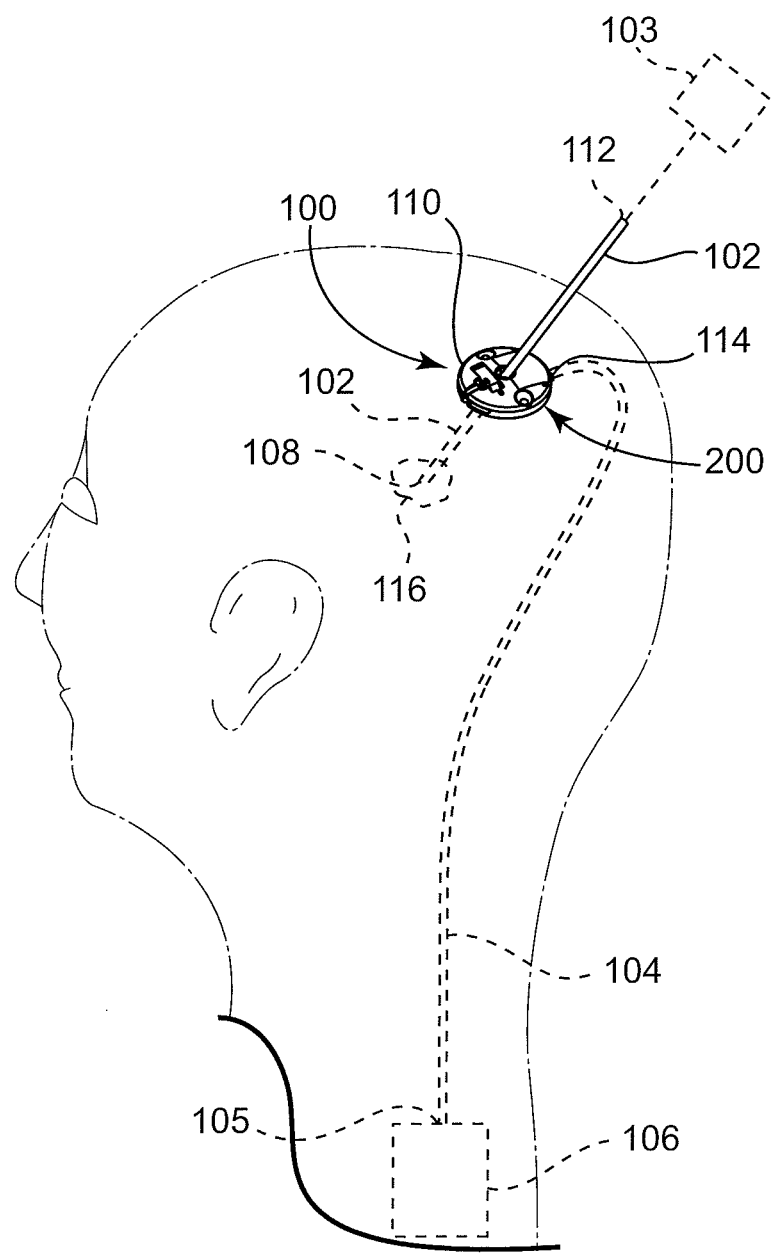
FIG. 1 is a diagrammatic view of a therapy delivery system in accordance with one embodiment of the invention, the system having a therapy delivery device (e.g., therapy catheter), an exemplary body portal anchor (e.g., a burr hole anchor), and, optionally, a therapy source (e.g., an infusion pump) and delivery or feed device (e.g., delivery catheter)

The figures are rendered primarily for clarity and, as a result, are not necessarily drawn to scale.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Embodiments of the instant invention may be directed to anchor devices and assemblies and to corresponding systems and methods for securing a therapy delivery device such as a therapy catheter relative to a body portal. For example, exemplary anchors described herein may be configured to secure a therapy delivery device such as an IPA therapy catheter routed through a cranial burr hole. These anchors may further incorporate components that permit the anchor itself to cut or trim the therapy catheter to the desired length during implantation. In other embodiments, exemplary anchors may incorporate interconnections such as fluid pathways to permit fluid coupling of the therapy catheter with a delivery catheter coupled to a feed port of the anchor. In still other embodiments, anchors may incorporate modular components that permit additional functionality, e.g., pressure monitoring, connections for multiple therapy catheters, etc.

Unlike with conventional anchor systems, anchors and systems in accordance with embodiments of the present invention may permit substantial isolation of the therapy catheter from bodily forces that may act outside of the body portal, e.g., forces acting upon the delivery catheter. Moreover, methods and anchor apparatus in accordance with embodiments of the present invention may substantially reduce or prevent movement of the therapy catheter tip during trimming as well as during securing and connecting of the delivery catheter with the therapy catheter. Various aspects of exemplary anchor devices, assemblies, systems, and methods are further described below.

Once again, in the described and illustrated embodiments, the anchor assembly is configured as a burr hole anchor that forms part of a system for infusing a therapeutic agent into the patient's brain via an IPA therapy catheter that passes through a burr hole formed in the skull. The anchor may be used to secure the catheter relative to the burr hole. However, while described herein in the context of burr hole anchors and corresponding infusion systems, anchor assemblies and systems in accordance with embodiments of the present invention may find use in other medical (and non-medical) applications that involve access through a portal. Moreover, while described herein with reference to an IPA therapy catheter, embodiments of the invention may find application to other catheters and to other fluid conveying devices, as well as to other therapy delivery devices, e.g., stimulation leads.

It is noted that the terms "comprises" and variations thereof do not have a limiting meaning where these terms appear in the accompanying description. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

FIG. 1 illustrates an exemplary implantable medical system, such as a brain infusion catheter system 100 as it may be configured during use, e.g., implantation.

The exemplary infusion system 100 may include a first medical tube, e.g., IPA therapy catheter 102, partially implanted within a mammalian brain 116. To assist with placement of the therapy catheter 102, a stereotactic apparatus, illustrated diagrammatically at 103, may be utilized. In the illustrated example, the therapy catheter 102 is implanted through a burr hole 110 (located underneath the burr hole anchor 200 in FIG. 1; see FIG. 2) such that its distal end 108 is located at a predetermined location within the brain 116.

A second medical tube, e.g., a feed or delivery catheter 104, may also be provided with a distal end 105 coupled to a therapy source or reservoir (e.g., an implantable infusion pump 106 such as a SynchroMed® II programmable infusion pump distributed by Medtronic, Inc., of Minneapolis, Minn. USA) containing a volume of the therapeutic agent. While described herein in the context of an implantable infusion pump 106, this configuration is not limiting. For example, other embodiments may replace the pump with most any internal or external medicament delivery device, e.g., syringe, drip bag, etc., without departing from the scope of the invention. FIG. 1 is intended to be a diagrammatic representation of an exemplary system. As a result, the illustration may not represent an actual snapshot of the system during or after implantation (e.g., the delivery catheter 104 may remain disconnected from the anchor until after the therapy catheter 102 is trimmed in accordance with any of the embodiments described herein).

A proximal end 112 of the therapy catheter 102 may be routable through a cranial burr hole anchor device or assembly (anchor devices and assemblies in accordance with exemplary embodiments of the present invention are referred to herein simply as "anchors"), see, e.g., burr hole anchor 200. In the illustrated embodiment, the therapy catheter 102 may, via the anchor 200, be operatively connected to a corresponding proximal end 114 of the delivery catheter 104 (e.g., via a connector, embodiments of which are described below). As used herein, the terms "distal" and "proximal" are taken from the reference of the anchor 200 as shown in FIG. 1. In at least one embodiment, the therapy catheter 102 may be made from a flexible material as further described herein.

The system 100 may, in one embodiment, be configured to deliver a therapeutic agent for the treatment of a chronic ailment, e.g., convection-enhanced delivery (CED) of a medicament for the treatment of Huntington's disease. The therapeutic agent is delivered, via the catheters 102 and 104, from the pump 106 to the brain 116. This application is not limiting, however, as the system may be configured to deliver other therapeutic agents (e.g., such as for the treatment of Parkinson's or Alzheimer's disease) to the brain or most any other anatomical area without departing from the scope of the invention.

With this general overview, the following description will address various embodiments and aspects of an exemplary infusion system 100, as well as methods for using the same. While these embodiments may be described with some degree of specificity, they are nonetheless intended to be exemplary. Those of skill in the art will recognize that other embodiments are certainly possible without departing from the scope of the invention.

Figure 2:
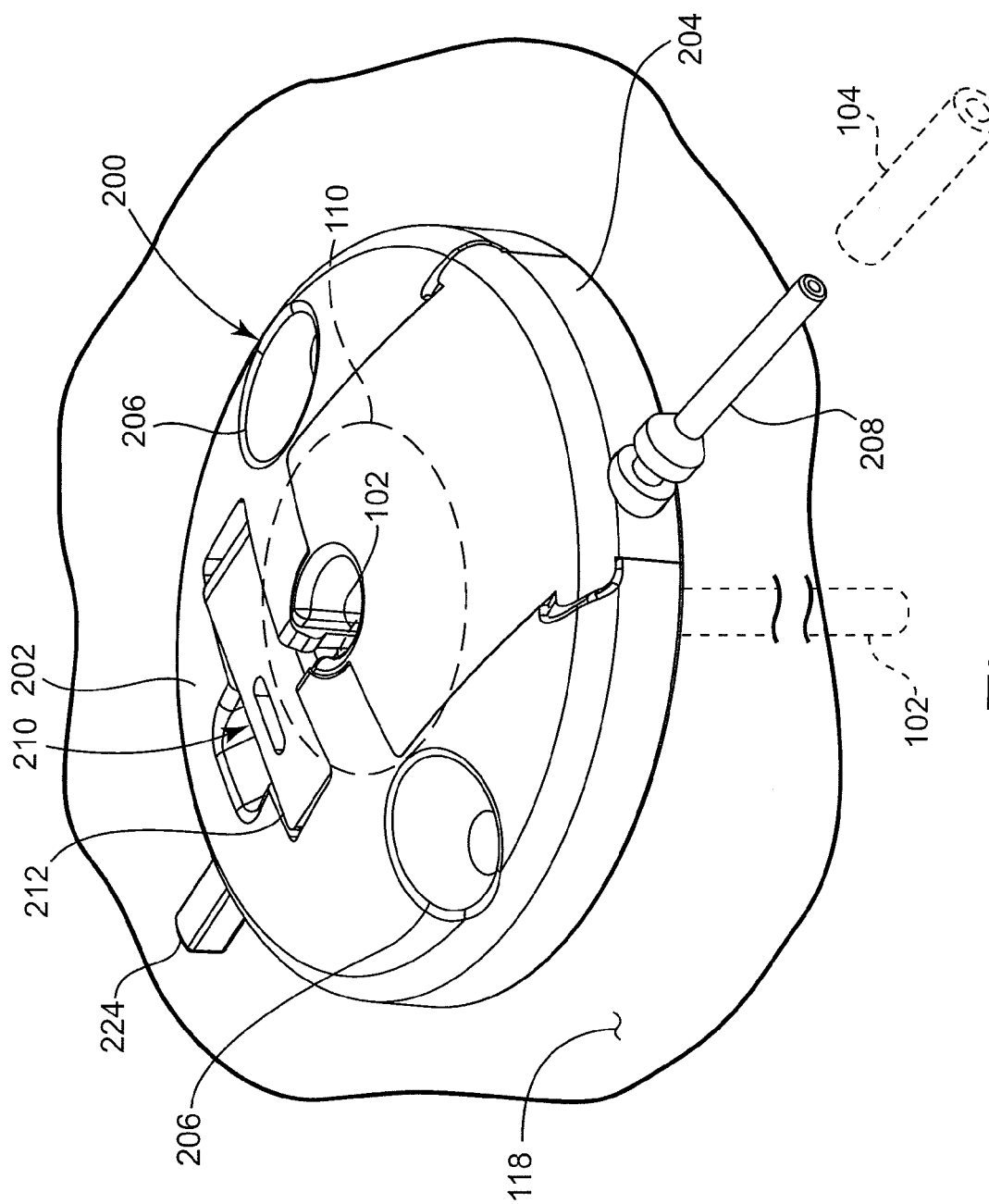
FIG. 2 is an enlarged perspective view of a burr hole anchor in accordance with one embodiment of the invention.

FIG. 2 illustrates an enlarged perspective view of an anchor system that includes not only the anchor or anchor assembly 200 illustrated in FIG. 1, but one or both of the catheters 102 and 104 as well. The anchor may include a base 202 and a module or insert 204 that together form a body of the anchor. The anchor 200 (e.g., the base 202) may be secured to bone 118 surrounding the burr hole 110, e.g., an outer surface of the skull, via any acceptable method, e.g., bone screws (not shown) extending through openings (e.g., screw holes 206) formed through the base 202.

The body of the anchor 200 may further include a delivery catheter feed pin 208 which, in one embodiment, extends outwardly from a peripheral edge of the anchor body, e.g., from the insert 204. The feed pin 208 may include a tubular male member that may be received within the lumen of the delivery catheter 104.

The anchor 200 may further include a catheter cutting or shearing mechanism 210. In one embodiment, the mechanism 210 is formed, at least in part, by a door 212 pivotally attached to the body, e.g., the base, and having a shearing edge described in more detail below.

Figure 3:
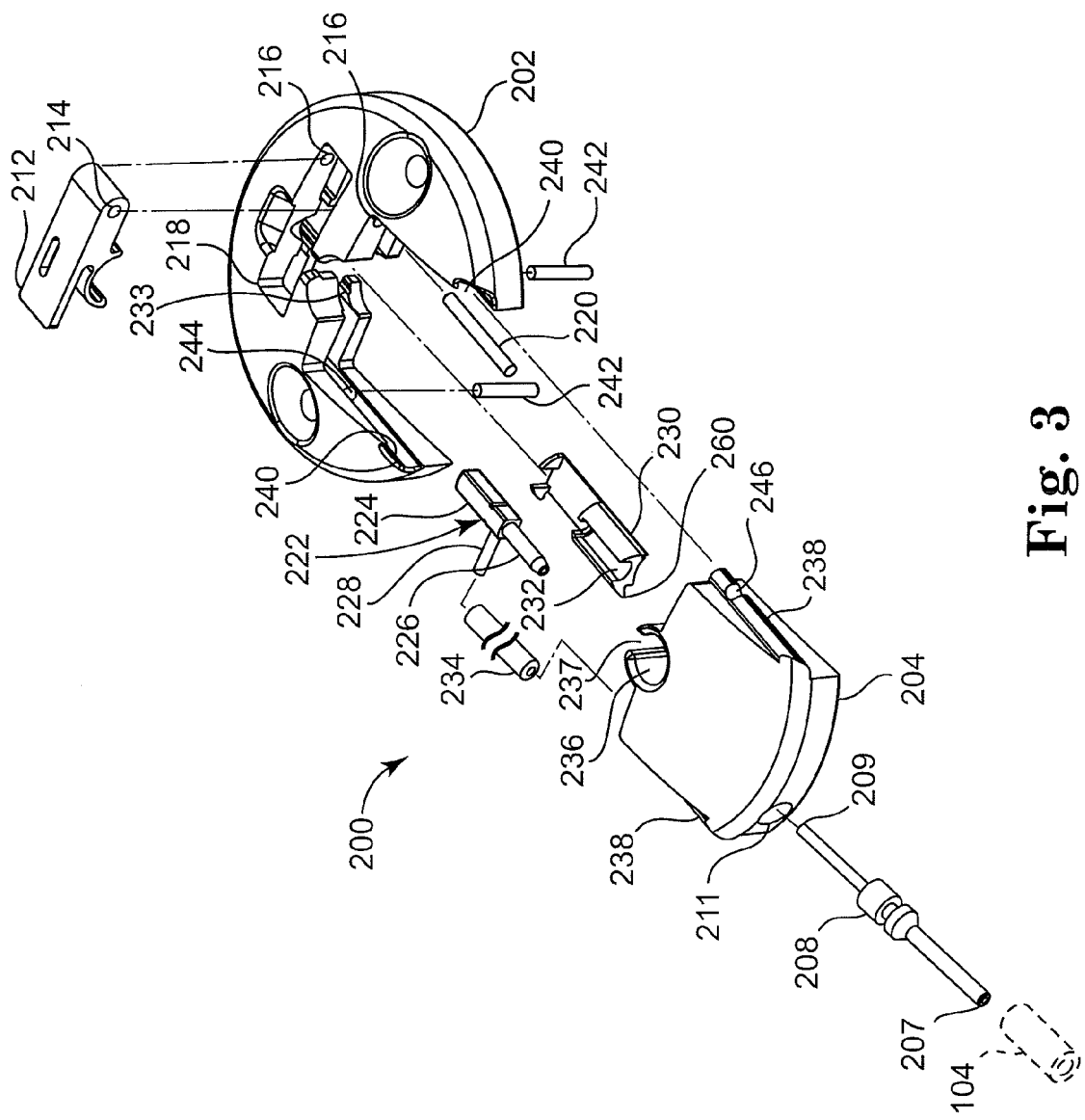
FIG. 3 is an exploded perspective view of the burr hole anchor of FIG. 2.

FIG. 3 illustrates the anchor 200 in an exploded perspective view. As clearly shown in this view, the shearing mechanism, e.g., door 212, may define an aperture or passageway 214. The body (e.g., the base 202) may include corresponding apertures or passageways 216 such that, when the door 212 is positioned within a receiving slot 218 formed in the body (e.g., in the base 202), a pin 220 may slide through the passageways 214 and 216 to secure the door relative to the slot for pivotal motion about an axis of the pin. The pin 220 may be secured in place by the module or insert 204 once the latter is attached as described below.

The anchor 200 may further include a therapy catheter connecting assembly (referred to herein simply as "connector 222") connected to the base 202. The connector 222 may include a push pin block or actuator 224, a therapy catheter feed pin 226, and a delivery or supply pin 228. The therapy catheter feed pin 226 and the supply pin 228 are, in one embodiment, in fluid communication with one another. That is, a lumen formed by the connector 222 may extend between the pins 226 and 228 such that fluid may flow between the two pins.

The anchor 200 (e.g., the body) may further include a guide 230 fixed relative to the base that supports and limits movement of the connector 222. For example, in the illustrated embodiment, the connector 222, and accordingly the therapy catheter feed pin 226, are operable to move (e.g., translate), relative to the base, between at least a first or uncoupled position and a second or coupled position. A trough 232 may be formed in the guide to receive and support the connector and assist with this translational movement.

In the first or uncoupled position, the therapy delivery device (e.g., the therapy catheter 102; see FIG. 2) is decoupled from the therapy source (e.g., the pump 106 of FIG. 1). Stated alternatively, when the connector 222 is in the uncoupled position, the connector (e.g., therapy catheter feed pin 226) may be detached or disconnected from the therapy catheter 102. However, when the connector 222 is in the second or coupled position, the connector (e.g., the therapy catheter feed pin 226) may be engaged with, or otherwise fluidly connected to, the therapy catheter 102 such that the latter is coupled to the pump 106. The actuator 224 may provide a convenient surface to assist the clinician with moving the connector 222 from the uncoupled position to the coupled position.

The guide 230 and connector 222 may be made of compatible materials to ensure satisfactory sliding of one component relative to the other. For example, in one embodiment, the connector 222 is made from grade 2 Titanium, while the guide 230 is made from grade 5 Titanium. However, other materials are certainly possible without departing from the scope of the invention.

The connector 222 may be placed into the guide 230 and the assembly slid into an opening 233 formed in the body (base 202). A stop (not shown) may be provided in the body to abut the guide when the guide is properly located. The connector 222 may then be secured in place once the insert 204 is attached to the base as described below. When the connector 222 is inserted properly into the base and configured in the first (uncoupled) position, the actuator 224 may protrude outwardly beyond the peripheral edge of the base as shown in FIG. 2.

FIG. 3 further illustrates the delivery catheter feed pin 208 detached from the body, e.g., from the insert 204. As shown in this view, the delivery catheter feed pin may include a first end 207 to engage the catheter 104, and a second end 209 that is received within an opening 211 of the insert 204. While most any retention technique is possible, the delivery catheter feed pin 208 may be secured within the opening 211, e.g., by welding, adhesive, press fit, or the like. In one embodiment, the pin 208 may be made from a relatively hard material, e.g., grade 2 Titanium.

To permit fluid passage from the delivery catheter 104 to the therapy catheter 102, the anchor assembly may further incorporate various fluid management, e.g., plumbing, features. For instance, a supply tube or conduit 234 (only partially illustrated in FIG. 3) may fluidly connect the supply pin 228 to the second end 209 of the delivery catheter feed pin 208. The conduit 234 may be made from a flexible material, e.g., 80 Shore A durometer urethane, to accommodate relative movement between the body and the insert 204. Accordingly, when the connector 222 is in the second or coupled position, therapeutic agent may flow from the delivery catheter 104, through the delivery catheter feed pin 208, supply conduit 234, supply pin 228, therapy catheter feed pin 226, and into the therapy catheter 102.

The body, e.g., the insert 204, may include a central opening 236 through which the therapy catheter 102 may extend (see, e.g., FIG. 1). A slot 237 may be formed through at least an upper portion of a wall of the opening 236 as shown in FIG. 3 (e.g., to yield a C-shaped opening when viewed from above the anchor) to permit the catheter 102 to pass from the opening 236 into the trough 232 as further described below. The body, e.g., inside surfaces of the slot 237, may define engagement surfaces operable to engage the therapy catheter 102 with a slight interference fit. Thus, the engagement surfaces may receive and cinch or immobilize the therapy catheter 102 passing through the burr hole.

While shown as having a base 202 defining a bay for receiving the module or insert 204, such a configuration is not limiting. For instance, in other embodiments, the body may be an integral component, e.g., with no removable insert. In yet other embodiments as described below, the base may define a frame for supporting multiple and interchangeable modules for specific applications.

Figure 4:
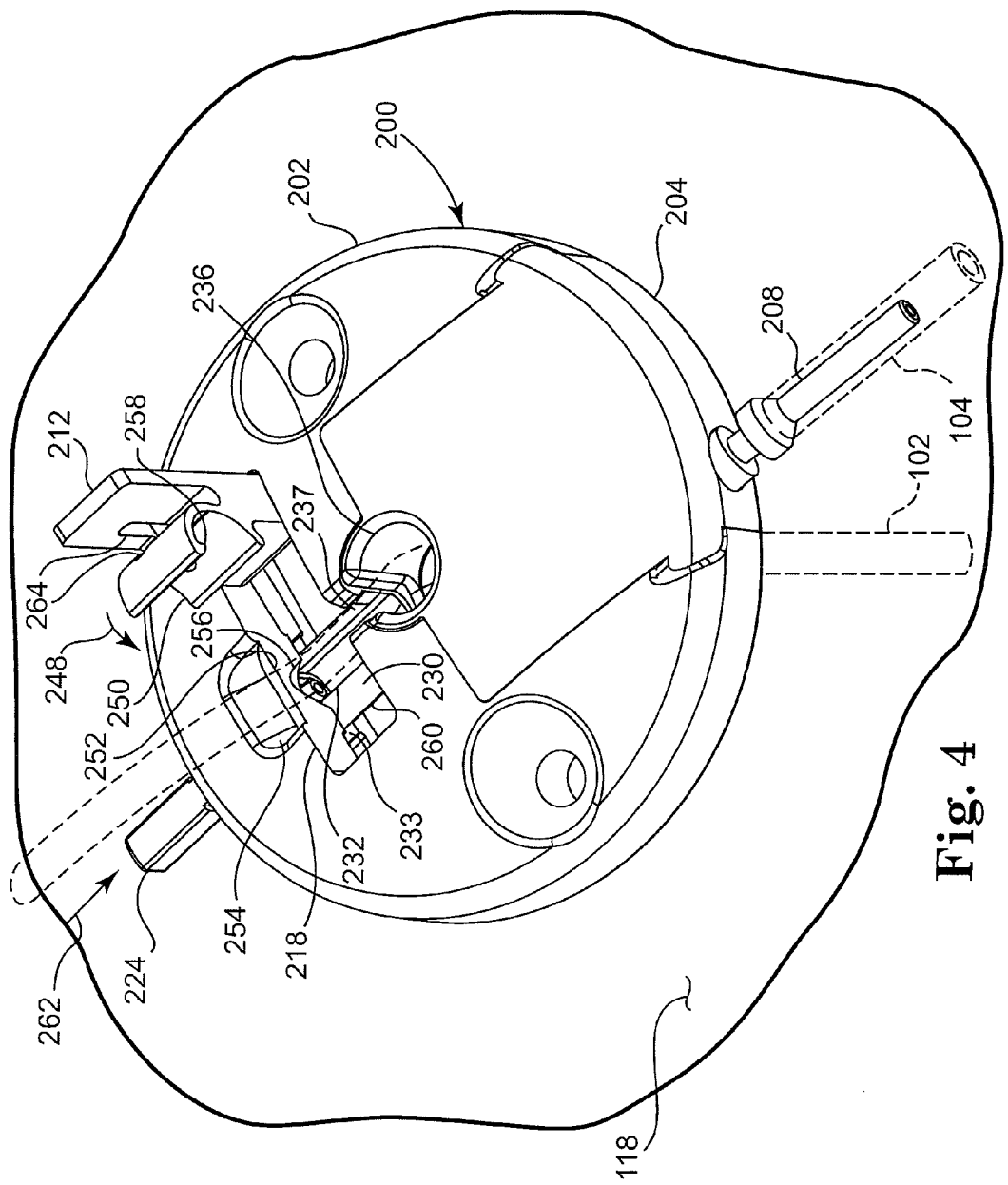
FIG. 4 is a perspective view of the anchor of FIG. 2 with a shearing mechanism, e.g., door, of the anchor shown in an open position.

The insert 204 may be assembled with the base 202 by engaging a tab 238 formed on one or more sides of the insert with corresponding slots 240 formed in the base. The insert 204, when filly inserted into the base as shown in FIG. 4, may secure the pin 220 (and thus the door 212) and the connecting assembly 222 in place. Moreover, the insert may be secured to the base by any number of techniques. In the illustrated embodiment, the insert 204 is secured to the base 202 with one or more connecting pins 242. The connecting pins 242 may be inserted through holes 244 (see also FIG. 6A) formed in the base. The holes 244 may align with holes or cutouts 246 (only one visible in FIG. 3) formed on the insert (e.g., on the tabs 238) when the insert is correctly attached to the base. That is, the connecting pins 242 may extend through the base and into the cutouts 246 to secure the insert relative to the base. The connecting pins 242 could be, for example, screw-in set screws, roll pins, or press fit pins.

FIG. 4 is a perspective view of the anchor 200 as assembled and positioned on the skull bone 118 over a burr hole (burr hole not visible in this view). The therapy catheter 102 is shown as already in place and the delivery catheter 104 is shown attached to the delivery catheter feed pin 208 (in some embodiments, the catheter 104 would not be attached to the feed pin 208 until after trimming and connecting of the therapy catheter 102 as further described below). Moreover, the shearing mechanism door 212 is illustrated in this view in a first or open position, and the connector 222 (see FIG. 3) is shown it its first or uncoupled position.

In use, the therapy catheter 102 may be correctly positioned through the burr hole and within the brain, e.g., via stereotactic equipment as represented in FIG. 1. In some embodiments, the therapy catheter may be routed through the central opening 236 of the preassembled anchor 200 before engagement with the stereotactic apparatus (and thus before implantation). As a result, once the catheter 102 is accurately located, the anchor may be positioned over the burr hole and attached to the skull bone 118 (e.g., with screws). The catheter 102 may then be disconnected from the stereotactic apparatus and bent to pass through the slot 237. The slot 237 may effectively cinch the therapy catheter 102 at a first point so that the therapy catheter is immobilized and lies within the adjacent portion of the trough 232 of the guide 230 as shown. At this point, the catheter 102 is effectively secured relative to the bone 118 surround the burr hole. When located in the trough 232, the catheter 102 is also prepared not only for shearing, but also aligned with the therapy catheter feed pin 226 of the connector 222 as further described below.

Figure 5:
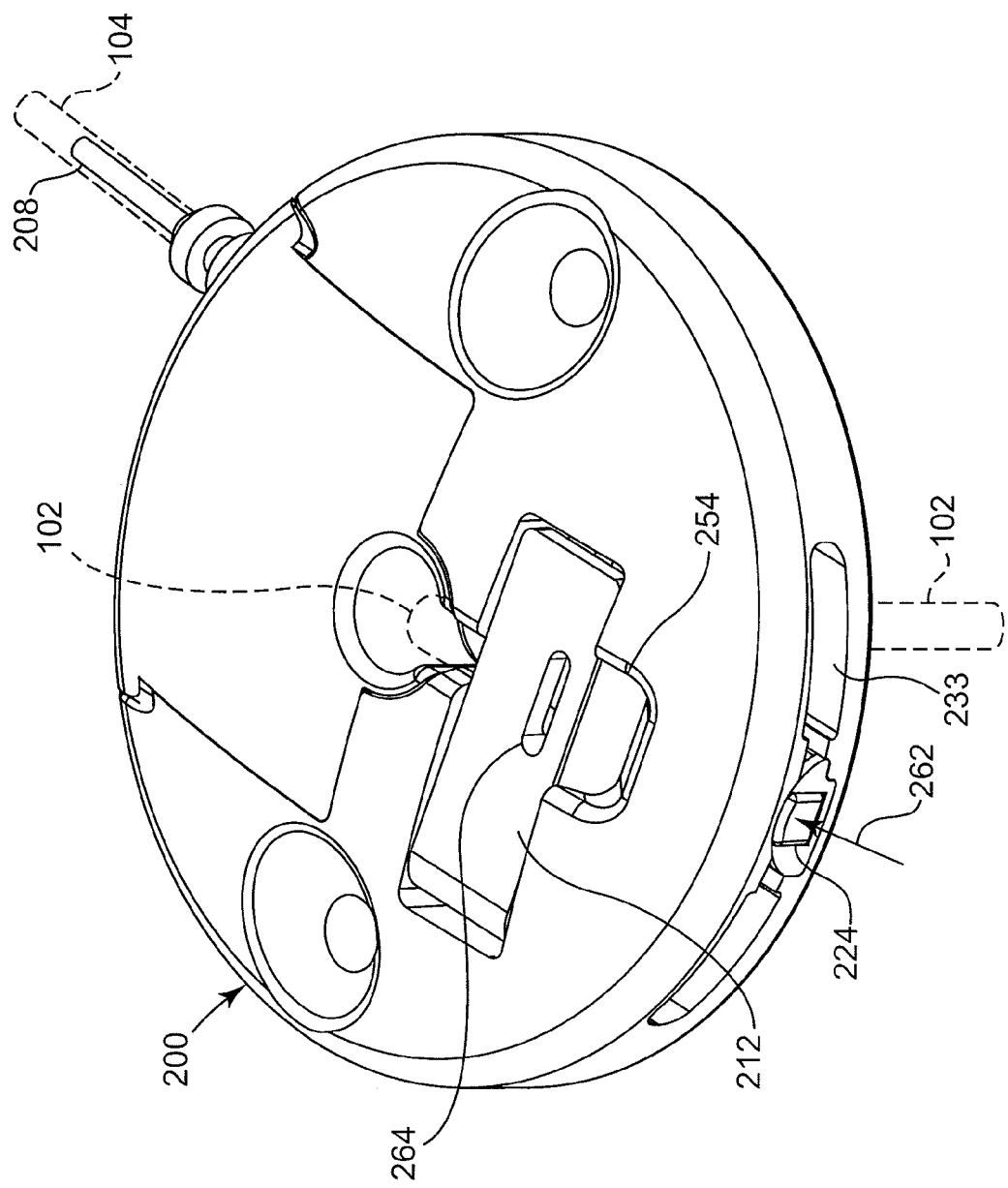
FIG. 5 is a perspective view of the apparatus of FIG. 2 with the door of the anchor shown in a closed position.

Once the therapy catheter 102 is located in the trough 232, the door 212 may be moved, e.g., pivoted in the direction 248 from the open position shown in FIG. 4, to a second or closed position as shown in FIG. 5. As the door closes, a first shearing edge 250 of the door passes in close proximity to a second shearing edge 252 defined by an edge of the receiving slot 218 of the body (e.g., of the base). In one embodiment, the door 212 and the body (e.g., both the base 202 and insert 204) are made from hard materials, e.g., grade 5 Titanium, to provide adequate shearing capability. Further, the door 212 and/or the slot 218 may be manufactured to close tolerances, e.g., wire cut, to ensure that the clearance between the width of the door and the width of the slot is minimal. For instance, in one embodiment, the clearance between the door 212 and the slot 218 is less than about 0.001 inches (in), e.g., about 0.0002 in, to assist with catheter cutting.

As the door 212 approaches the second position shown in FIG. 5, the shearing edges 250 and 252 shear the therapy catheter 102. To assist with shearing, the body may form a depression 254 on the top surface of the body to form a sharper angle along the cutting surface. The depression 254 may also allow locating the shearing edge 252 closer to the trough 232, a feature that may assist with reducing therapy catheter movement during the cutting process. A relief 256 (see FIG. 4) below the shearing edge 252 may assist the cut face of the catheter with opening back up after potential flattening in the shearing process.

When the door reaches the second closed position, the catheter 102 is cut and that excess portion of the catheter beyond the shearing edges 250, 252 may be discarded. Moreover, the door 212 may include a semi-cylindrical cutting surface that wraps around the guide 230 and helps guide the catheter into the trough 232. To ensure that the door 212 closes completely, a snap-fit tab 258 (see FIG. 4) may be provided which engages a lip 260 of the guide when the door is fully closed.

With the door 212 now in the second closed position of FIG. 5, the actuator 224 of the connector 222 may be pushed inwardly, e.g., in the direction 262 shown in FIGS. 4 and 5. As the connector 222 is pushed inwardly (e.g., in a direction radially to the anchor), the therapy catheter feed pin 226 may be inserted into the proximal end of the therapy catheter 102, thereby permitting fluid to pass (from the delivery catheter 104) through the therapy catheter feed pin 226 and into the therapy catheter. The door 212 may include one or more viewing portals or windows 264 that permit the clinician to observe the therapy catheter feed pin 226 and ensure that it moves into the lumen of the catheter 102 as desired. In the illustrated embodiment, friction between the therapy catheter feed pin 226 and the catheter 102 may be sufficient to ensure that the therapy catheter feed pin remains in place. If desired, the door 212 may be opened to examine the connection between the feed pin 226 and the therapy catheter 102. The connector 222 may, when in the second position illustrated in FIG. 5, be contained within the peripheral envelope defined by the anchor 200, e.g., the actuator 224 may be configured such that it does not protrude beyond the peripheral edge of the anchor. This may reduce or eliminate exposed surfaces that a bodily force could act upon to pull the connector 222 out of the anchor.

Figure 6B:
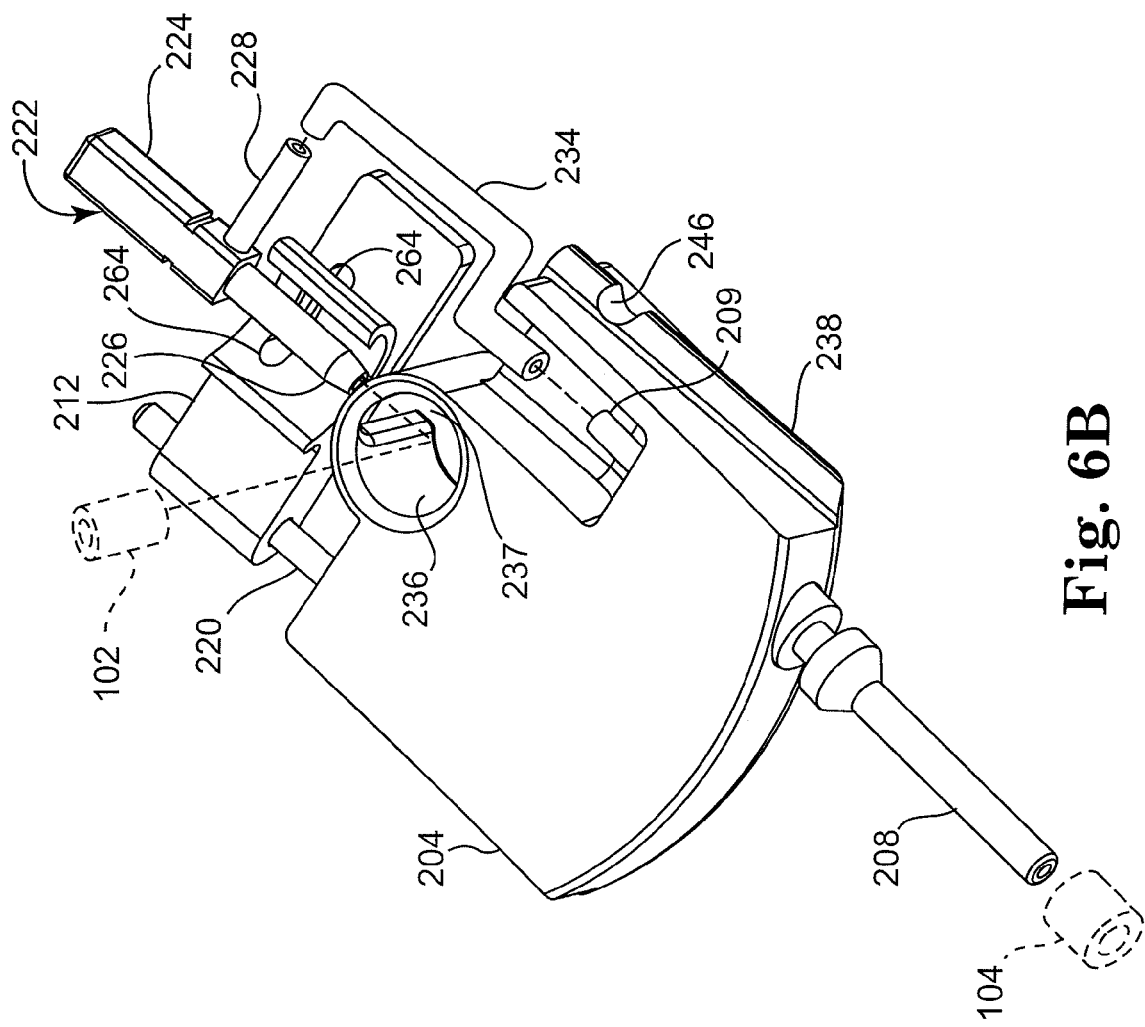

FIG. 6A illustrates a bottom perspective view of the anchor 200 (with the therapy catheter removed for clarity), and FIG. 6B illustrates an exploded bottom perspective view of the module or insert 204 of the anchor. As illustrated in these views, the supply conduit 234 may connect the second end 209 of the delivery catheter feed pin 208 with the supply pin 228 of the connector 222 (see also FIG. 3). As a result, fluid may flow from the delivery catheter 104 to the therapy catheter 102 (when the therapy catheter feed pin 226 is coupled to the catheter 102 as described above). In one embodiment, the supply conduit 234 is medical grade micro polyurethane tubing, e.g., having an inner diameter of about 0.012 in and an outer diameter of about 0.025 in.

Although not described herein, those of skill in the art will realize that the various components and catheters, e.g., catheters 102 and 104, of the system of FIG. 2 (as well as those of FIGS. 7 and 12) may be primed or otherwise purged of air prior to completion of implantation in accordance with known methods.

Figure 7:
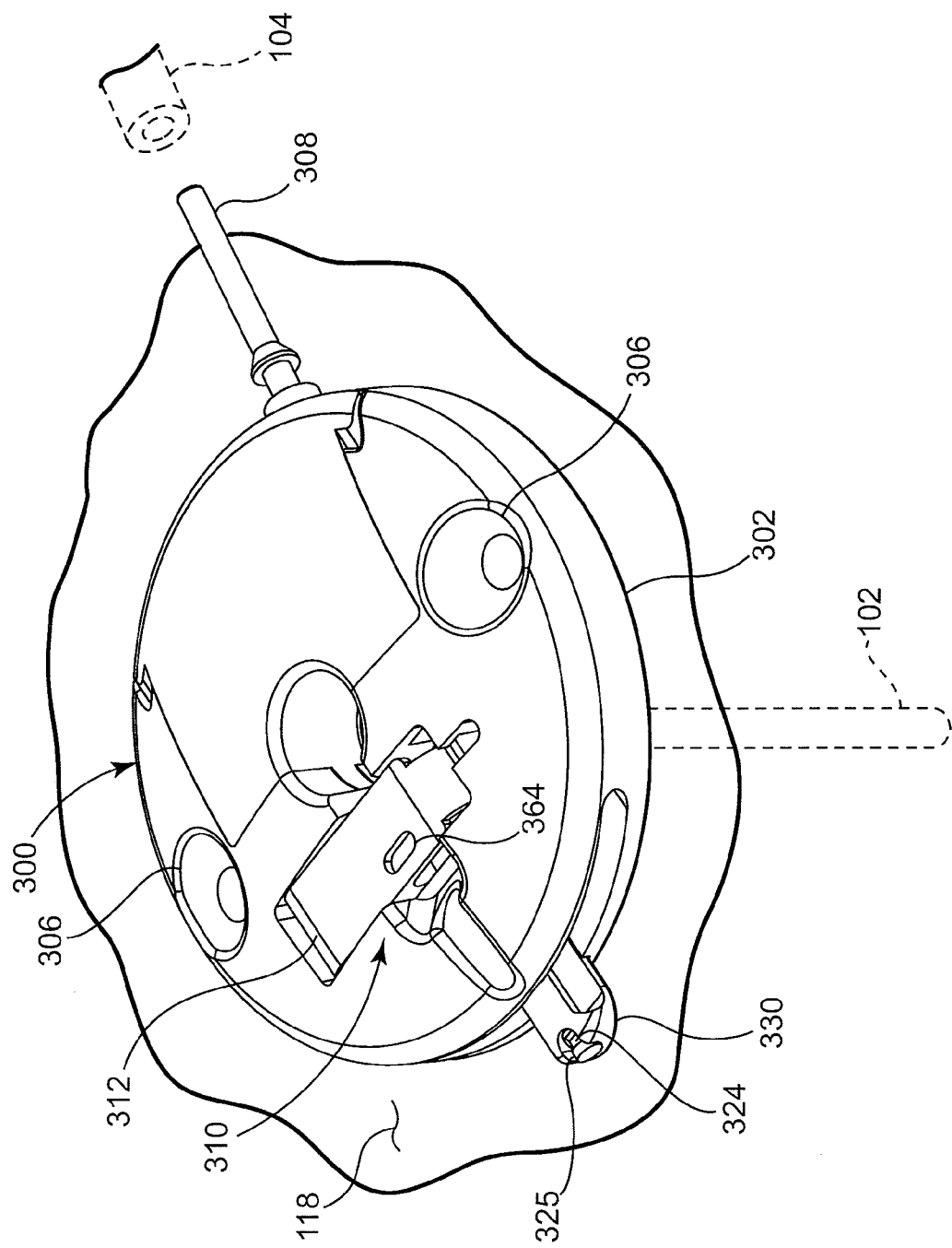
FIG. 7 is an enlarged perspective view of a burr hole anchor in accordance with another embodiment of the invention.

FIG. 7 illustrates an enlarged perspective view of an anchor assembly (e.g., anchor 300) in accordance with another embodiment of the invention. The anchor 300 is similar in many respects to the anchor 200 already described and illustrated herein and may be used in place of the anchor 200 in various applications. As a result, where the description of various components and/or aspects of the anchor 300 would be duplicative in view of the description provided herein above of the anchor 200, such description may not be repeated below.

The anchor 300 may, like the anchor 200, include a base 302 and a module or insert 304 (see FIG. 8) that together form a body of the anchor. The anchor 300 may be secured to tissue such as bone surrounding the burr hole, e.g., an outer surface of the skull bone 118 (see FIG. 2), via any acceptable method, e.g., bone screws (not shown) extending through openings 306 formed through the base 302.

The anchor 300 may further include a delivery catheter feed pin 308 similar to the delivery catheter feed pin 208. The delivery catheter feed pin 308 may include a tubular male portion or member that may be received by the delivery catheter 104.

The anchor 300 may further include a catheter cutting or shearing mechanism 310 similar in many respects to the mechanism 210 described above, e.g., it includes a door 312 pivotally attached to the body and having a first shearing edge.

Figure 8:
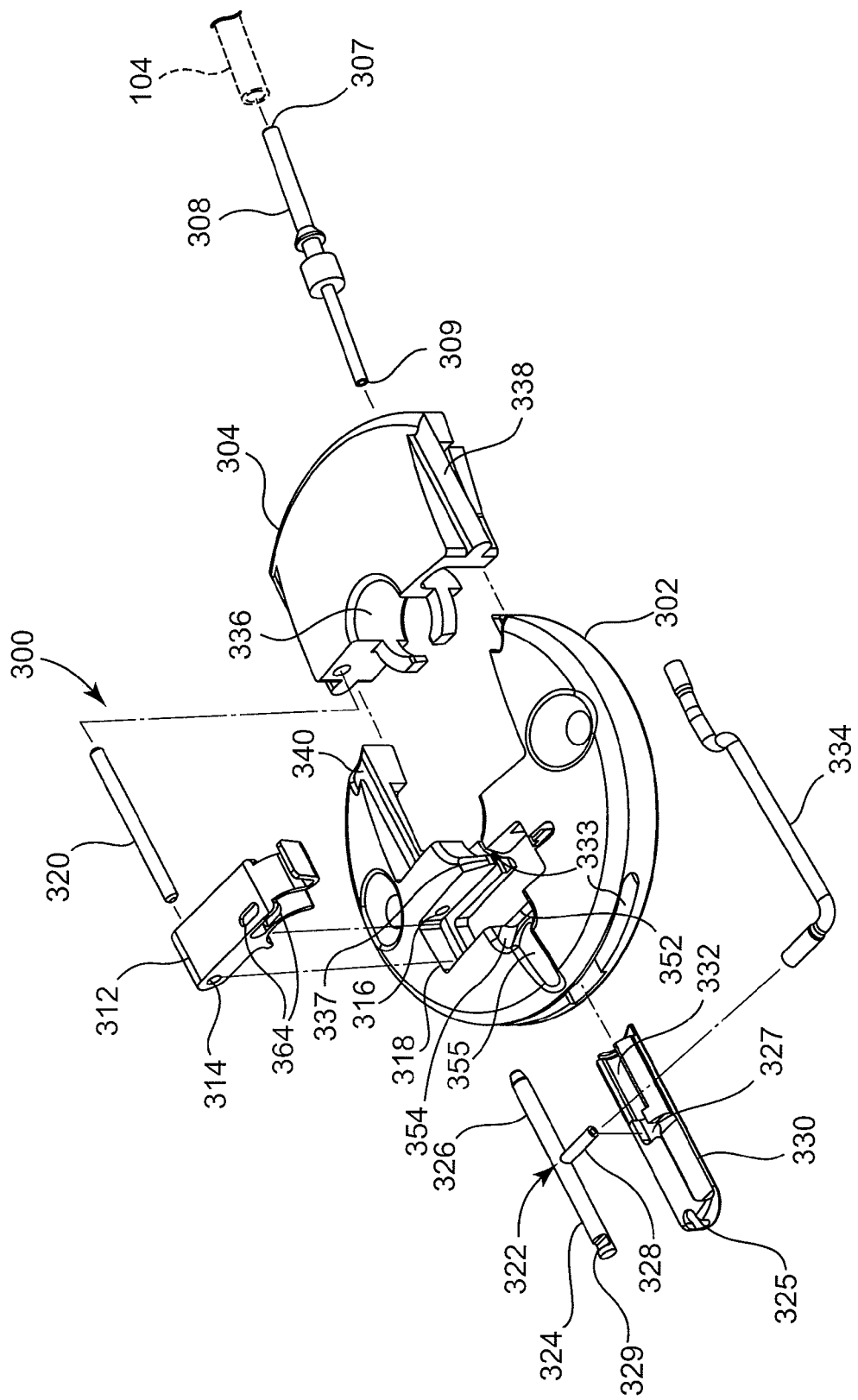
FIG. 8 is an exploded perspective view of the anchor of FIG. 7.

FIG. 8 illustrates the anchor 300 in an exploded perspective view. As shown in this view, the door 312 (like the door 212) may be pivotally attached to the body (e.g., to the base 302) within a receiving slot 318 via a pin 320 that passes through passageways 314 and 316 formed in the door and base, respectively. The pin 320 may be secured in place by the insert 304 once the latter is attached to the base.

The anchor 300 may further include a therapy catheter connecting assembly or connector 322. The connector 322, like the connector 222, may include an actuator 324, a therapy catheter feed pin 326, and a supply pin 328. The therapy catheter feed pin 326 and the supply pin 328 are fluidly coupled to one another in like fashion to the connector 222.

Figure 11A:
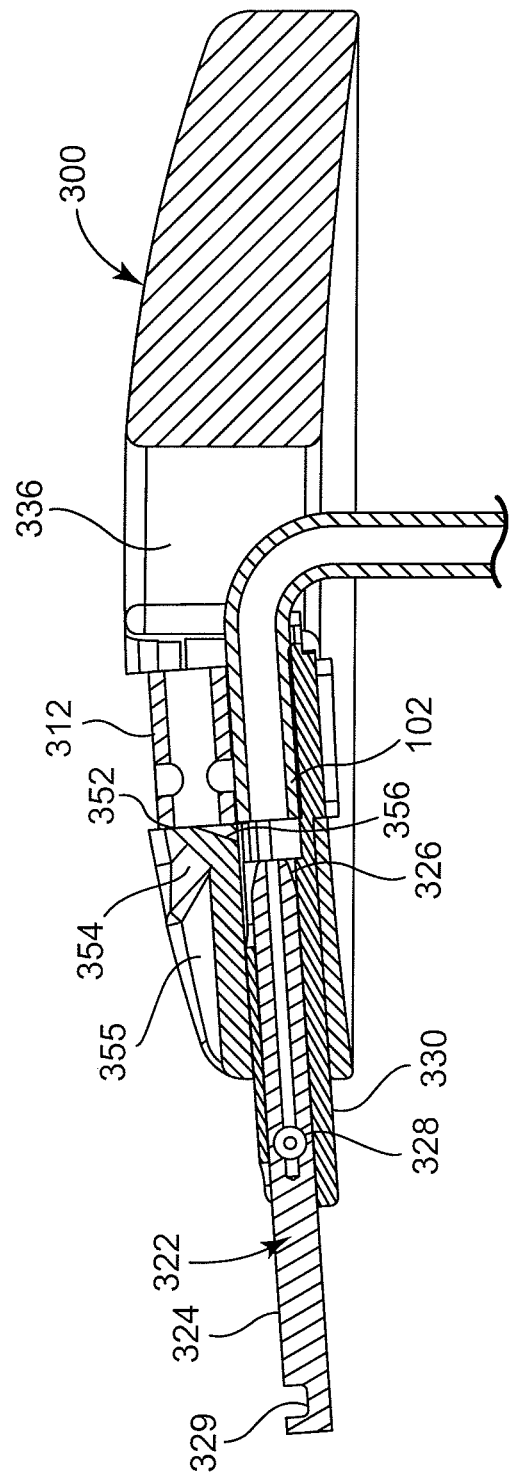

The anchor 300 may further include a guide 330 to support and limit movement of the connector 322 in a fashion similar to the guide 230 described above. Accordingly, in one embodiment, the connector 322 may move, e.g., translate along a trough 332 formed in the guide 330, between a first or uncoupled position and a second or coupled position substantially like the connector 222 described above. Once again, in the first or uncoupled position, the connector, e.g., the therapy catheter feed pin 326, may be detached or disconnected from the therapy catheter 102 as shown in FIG. 11A. However, when the connector 322 is in the second or coupled position, the connector, e.g., the therapy catheter feed pin 326, may be fluidly connected to the therapy catheter 102 as further described below and illustrated in FIG. 11B.

The guide 330 and connector 322 may be configured differently than the like components of the anchor 200. For instance, the guide 330 may be slotted to more positively retain the connector 322, a feature that may also improve ease of assembly. In one embodiment, this may be accomplished by providing an outer guide hole 325 and a right angle slot 327 as shown in FIG. 8. As a result of these features, the connector 322 may be inserted (e.g., from the right in FIG. 8) into the trough 332 with the supply pin 328 extending upwardly. The connector 322 may then be slid (to the left in FIG. 8) within the trough until the supply pin 328 reaches the right angle slot 327. At this point, the connector 322 may be rotated until the supply pin 328 reaches the longitudinal portion of the right angle slot 327 in a movement similar to that of a bolt action rifle. The connector 322 may then continue to translate to the left (such that the actuator 324 passes through the outer guide hole 325) until the supply pin 328 contacts a stop surface of the guide proximate the outer guide hole.

The connector 322 seated within the guide 330 may be slid into an opening 333 formed in the base 302 (e.g., from the inner side (right side in FIG. 8) of the base 302) until the guide abuts a stop portion (not shown) in the base. As with the connector 222, the connector 322 may be secured in place once the insert 304 is attached to the base 302. When the insert 304 is attached to the base 302, the resulting body, e.g., the base 302 and/or insert 304, may define a central opening 336 through which the therapy catheter 102 may pass. Further, a slot 337 may be formed through at least a portion of the body (e.g., the base 302). When the insert 304 is connected to the base 302, the slot 337 may permit access to the opening 336 to permit the therapy catheter 102 to pass from the opening 336 into the trough 332 as further described below. The inside surfaces of the slot 337 may form engagement surfaces configured to receive and immobilize the therapy catheter 102. For instance, the engagement surfaces may receive and immobilize the catheter 102 passing through the burr hole with a slight interference fit.

Figure 9:
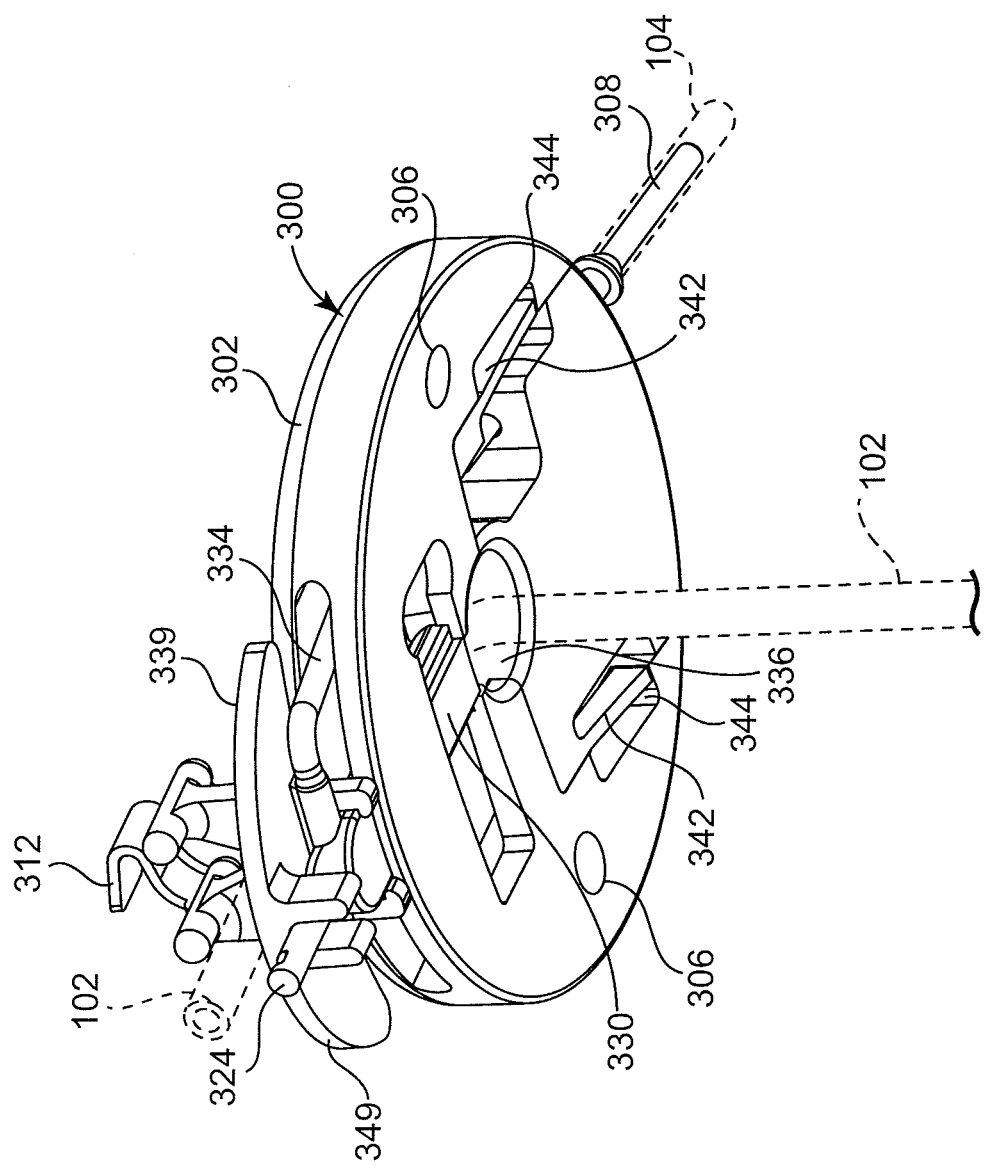
FIG. 9 is a bottom perspective view of the anchor of FIG. 7 with a clip attached.

When the connector 322 is inserted properly into the body (e.g., into the base 302) and configured in the first or uncoupled position, the actuator 324 of the connector 322, as well as the guide 330 itself, may protrude outwardly beyond the peripheral edge of the base 302 as shown in FIG. 9.

FIG. 8 further illustrates the delivery catheter feed pin 308 detached from the insert 304. As shown in this view, the feed pin may include a first end 307 to receive and engage the catheter 104, and a second end 309 that is received within an opening (not visible) of the insert 304.

A supply conduit 334 may interconnect the supply pin 328 to the second end 309 of the delivery catheter feed pin 308. Accordingly, when the connector 322 is in the second or coupled position as described below, therapeutic agent may flow from the delivery catheter 104, through the delivery catheter feed pin 308, supply conduit 334, supply pin 328, therapy catheter feed pin 326, and into the therapy catheter 102.

As with the insert 204, the insert 304 may be assembled with the base 302 by engaging a tab 338 formed on one or more sides of the insert with corresponding slots 340 formed in the base. The insert 304, when fully inserted into the base 302 (as shown in FIG. 9), may secure the pin 320 (and thus the door 312) and the connecting assembly 322 in place. Moreover, the insert may be secured to the base in a manner described above with respect to the base 202 and insert 204. Alternatively, the insert 304 may be secured to the base 302 using one or more locking tabs 342 as shown in FIG. 9. The locking tabs 342 may be malleable such that after the insert 304 is assembled into the base 302, the tabs 342 may be bent outwardly with a tool (e.g., forceps or the like, etc.) such that the tabs 342 engage locking surfaces 344 defined by the base 302 (tabs 342 shown in an outward, locked position in FIG. 9). To remove the insert 304, the locking tabs 342 may be moved inwardly such that locking tabs 342 are not engaged with the locking surfaces 344. In another embodiment, the locking tabs 342 may be formed of a resilient material and biased outwardly such that a snap-fit is formed between the locking tabs 342 and locking surfaces 344. As shown, the locking tabs 342 are part of the insert 304; however, in other embodiments, the locking tabs may be part of the base 302 and may engage corresponding locking surfaces on the insert 304.

FIG. 9 illustrates a lower perspective view of the anchor before trimming of the therapy catheter 102 and prior to fluid coupling of the therapy catheter to the feed catheter 104. As shown in this view, a removable clip 339 may be provided. The clip 339, which may in one embodiment be made from polysulfone or similar material, may include two legs that straddle the guide 330 when the connector 322 is in the first position as shown, and prevent the connector 322 from traveling inwardly towards its second position, e.g., by interfering with movement of the supply pin 328. Accordingly, the supply pin 328, and thus the therapy catheter feed pin 326, may remain positively retracted during the cutting operation. The clip 339 may also include a protective portion or wing 349 that extends beyond the exposed portion of the supply conduit 334 and supply pin 328. The clip 339 may provide additional advantages as described in more detail below.

Figure 10A:
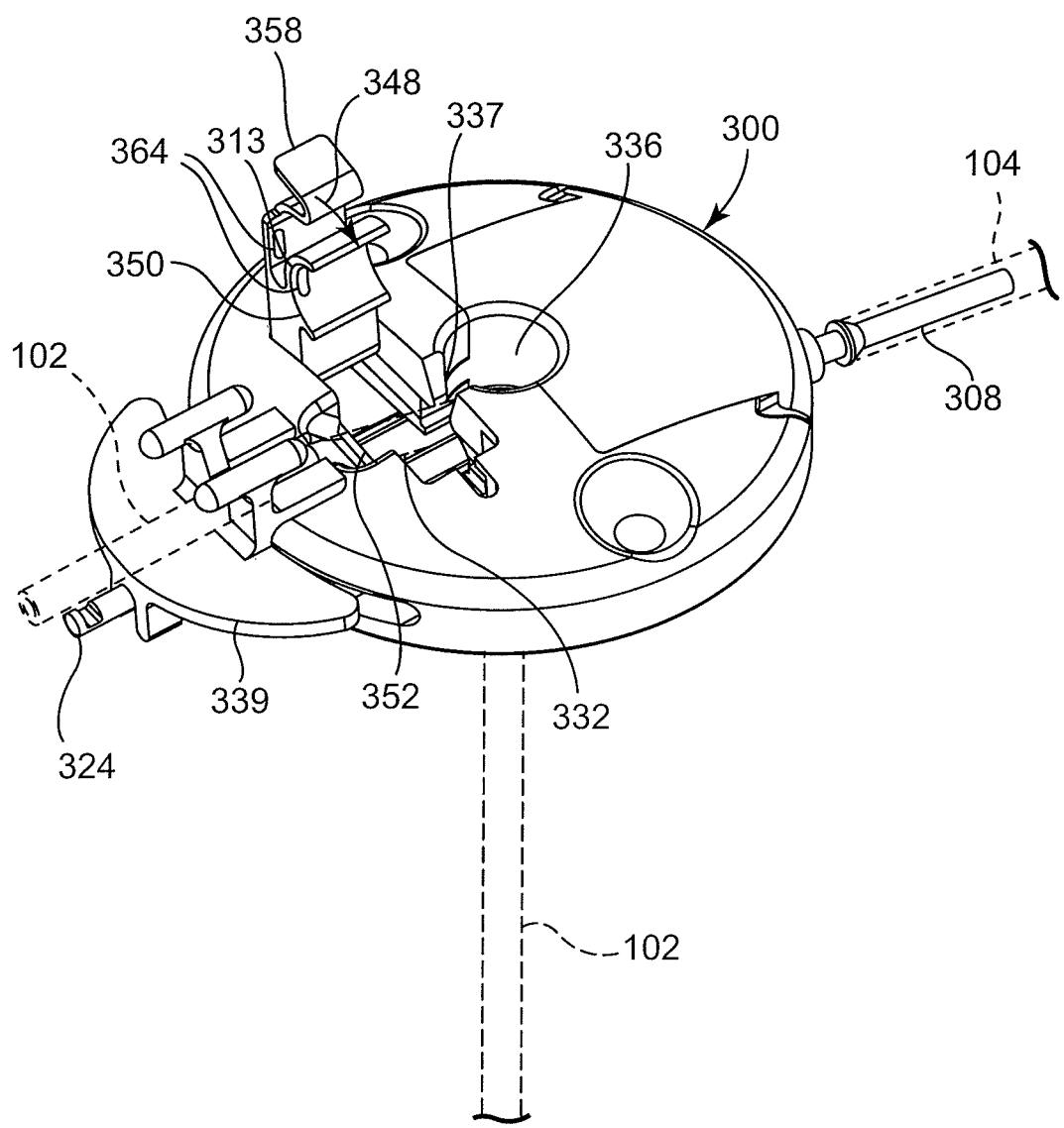
Figure 10B:
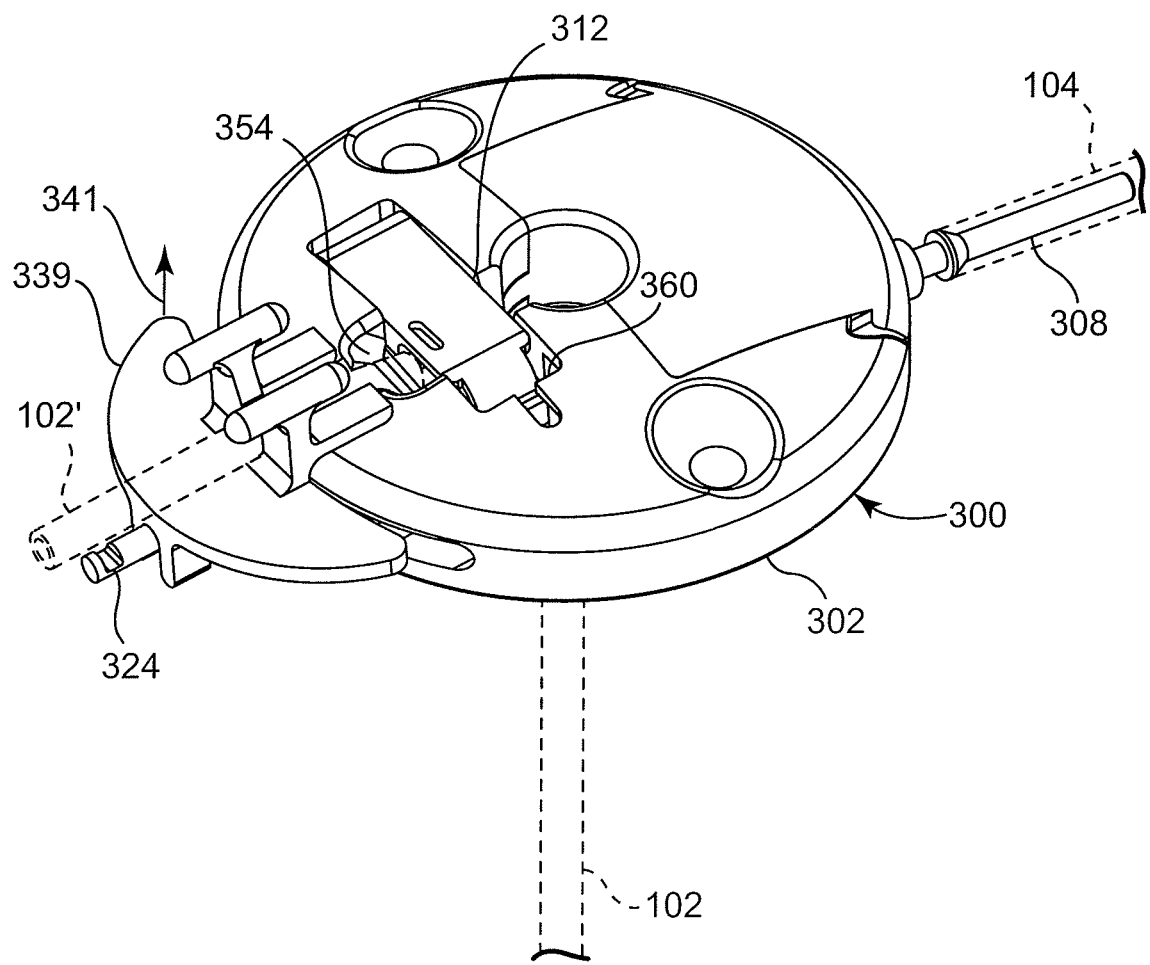
Figure 10C:
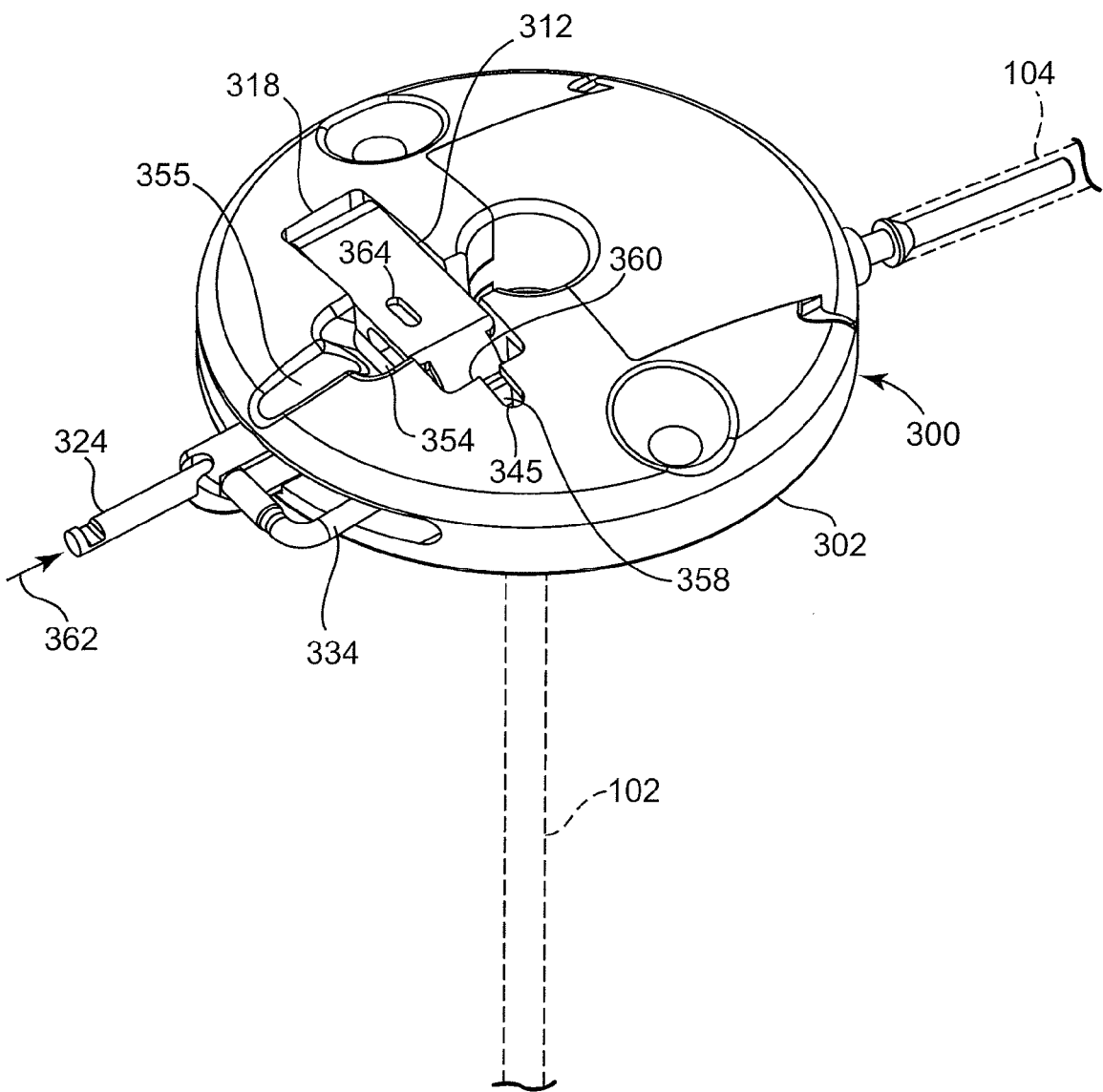
FIG. 10C is a perspective view with the door shown in a closed position and the clip removed.

FIGS. 10A-10C are perspective views of the anchor 300 as assembled and positioned on the skull bone 118 over a burr hole (not viewable). The therapy catheter 102 is shown as already in place and the delivery catheter 104 is show as it may be attached to the delivery catheter feed pin 308 (once again, the connection of the delivery catheter may not occur until after the therapy catheter is trimmed and connected). Moreover, the cutting mechanism, e.g., door 312, illustrated in FIG. 10A is in a first or open position, and the connector 322 is shown in its first or uncoupled position.

In use, the catheter 102 may be correctly positioned within the brain, e.g., via stereotactic equipment and the anchor secured to the skull as already described above. The therapy catheter 102 may then be routed through the opening 336 such that its free end lies in or near the trough 332 of the guide 330 as shown in FIG. 10A. This may be accomplished by gripping or cinching the catheter 102 within the slot 337 (e.g., a first catheter cinch point) such that the catheter lies within the portion of the trough 332 near the slot. Once the therapy catheter 102 is located in or near the trough 332 as shown in FIG. 10A, the clip 339 may receive and retain the free excess portion or end of the catheter 102 as shown (e.g., the clip 339 may form a second catheter cinch point to hold the catheter during cutting). By utilizing the clip 339, the catheter 102 may be held in the desired location over the trough 332 during the cutting process. This desired location aligns the catheter 102 directly over the trough 332, which assists with reducing pinching between the door 312 and the outer surface of the trough. Moreover, by securing the free end of the catheter 102 in the clip 339 before trimming, potential loss of the cut excess portion of the catheter after trimming is minimized. In one embodiment, the two cinch points, e.g., the slot 337 and the clip 339, may further hold the catheter 102 close to the trough 332 to further reduce the potential for catheter movement during trimming and/or connection.

Once the catheter 102 is secured within the clip 339, the catheter is firmly held between first and second shearing edges 350 and 352, respectively. The door 312 may then be moved, e.g., pivoted by the clinician in the direction 348 from the open position shown in FIG. 10A, to a second or closed position as shown in FIG. 10B. As the door 312 closes, the first shearing edge 350 (see FIG. 10A) of the door 312 passes in close proximity to the second shearing edge 352 defined by an edge of the receiving slot 318. The door 312 and the body (i.e., base 302) may be constructed in a manner similar to that described above with respect to the door 212 and base 202.

As the door 312 approaches the second position shown in FIG. 10B, the shearing edges 350 and 352 may shear the therapy catheter 102, leaving the excess severed portion or tip 102' of the catheter gripped within the clip 339.

To assist with shearing and to assist with immobilizing the therapy catheter 102, the body (e.g., the base 302) may form a depression 354 and a channel 355 (see FIG. 10C) on the upper surface, as well as a relief 356 (see FIG. 11A) below the shearing edge 352. The depression 354 (adjacent the second shearing edge 352) and channel 355 (adjacent the depression) may receive the catheter 102 such that it is close to the trough 332 prior to cutting to assist with minimizing catheter movement during the cutting process. As with the door 212, the door 312 may include a semi-cylindrical cap 313 (see FIG. 10A) that surrounds the catheter and constrains it by compression against the guide 330. To ensure that the door closes completely and remains closed, the door may form a snap-fit tab 358 (see also FIG. 10A) that engages a lip 360 of the body (e.g., the base 302) when the door is fully closed as shown in FIG. 10B. This snap fit feature may be advantageous in that it provides feedback (e.g., visual and/or audible) to the clinician that the door 312 is snapped completely shut.

When the door reaches the second closed position, the catheter 102 is cut and the clip 339, which retains the excess cut portion 102', may be removed from the body of the anchor. In one embodiment, the portion 102' may be removed by lifting the clip 339 upwardly, e.g., in the direction 341 as shown in FIG. 10B, and separating the clip 339 (and thus the portion 102') from the anchor 300.

FIG. 10C illustrates the anchor with the clip 339 and excess catheter portion 102' removed. With the door 312 in the second closed position, the actuator 324 of the connector 322 may be pushed by the clinician radially inwardly, e.g., in the direction 362, from the uncoupled position to the coupled position. As the connector 322 is pushed inwardly, the therapy catheter feed pin 326 (see FIG. 8) is forced into the proximal end of the therapy catheter 102, thereby permitting fluid to pass through the therapy catheter feed pin 326 and into the therapy catheter. The door 312 may include one or more viewing portals or windows 364 that permit the clinician to observe the feed pin 326 and ensure that it moves into the lumen of the catheter 102 as desired. The connector 322 may, when in the second or coupled position illustrated in FIG. 7, be contained within the peripheral envelope defined by the guide 330.

If desired, the door 312 may be opened to verify the connection of the therapy catheter feed pin 326 with the therapy catheter 102. To open the door 312, a slot 345 may be formed in the base 302 adjacent the receiving slot 318 as shown in FIG. 10C. By inserting a tool (e.g., forceps) into the slot 345, the tab 358 of the door 312 (see FIG. 10A) may be deflected sufficiently to permit the door to return to its open position. In addition to connection verification, the clinician may open the door for other reasons including, for example, performing a manual connection with the catheter.

Figure 11B:
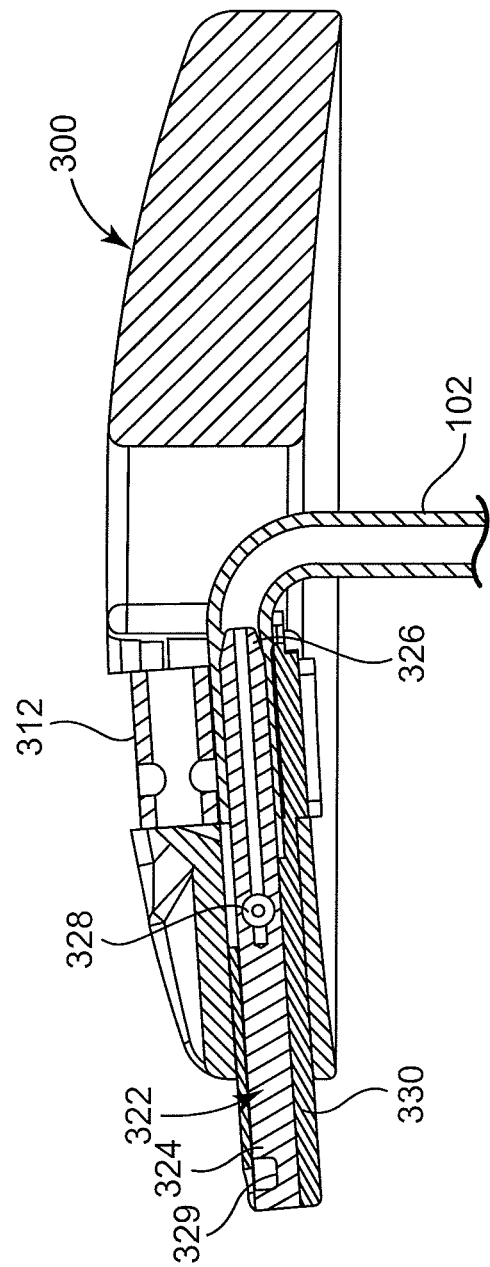

If the insertion of the therapy catheter feed pin 326 is unsatisfactory (e.g., poor connection with therapy catheter, no connection with the therapy catheter, etc.), the clinician may engage a tool (e.g., forceps) with a notch 329 (see FIGS. 11A and 11B) formed on the actuator 324 of the connector 322 and pull outwardly, thereby returning the connector 322 to the first, uncoupled position. If the therapy catheter feed pin 326 had been connected with the therapy catheter 102, then such outward movement of the connector 322 would remove the therapy catheter feed pin 326 from the therapy catheter 102. After the connector 322 has been moved into the first, uncoupled position, a connection may again be attempted between the therapy catheter feed pin 326 and the therapy catheter 102 by moving the connector 322 (e.g., the actuator 324) back into the second, coupled position. FIGS. 11A and 11B illustrate cross sectional views of the anchor 300 (anchor 200 would appear similar), wherein FIG. 11A illustrates the anchor with the connector 322 in its first uncoupled position, and FIG. 11B illustrates the same view with the connector in the second coupled position. When the connector 322 is in the position shown in FIG. 11B, fluid may flow from the delivery catheter 104 to the therapy catheter 102.

Figure 12:
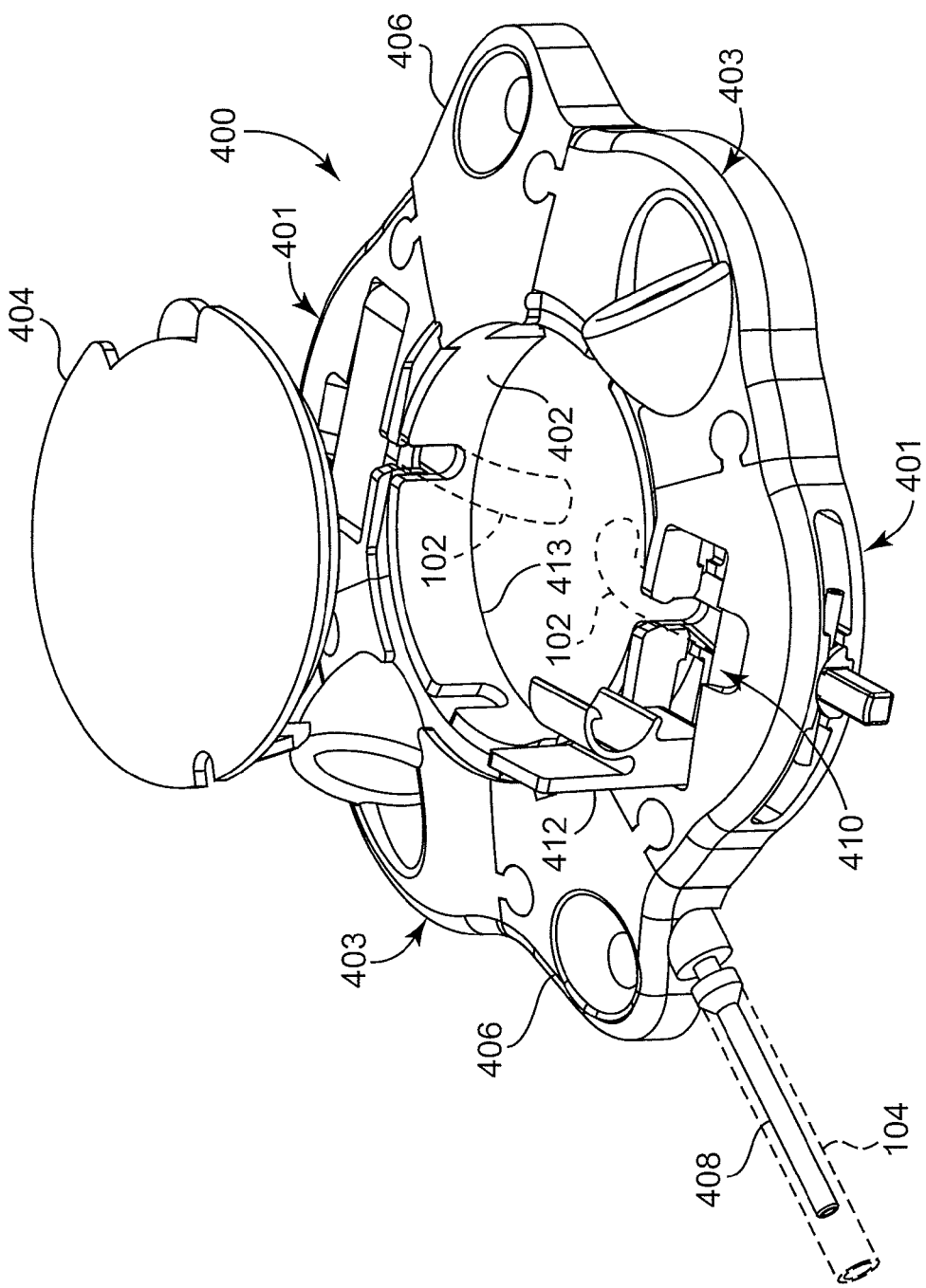
FIG. 12 is a perspective view of a burr hole anchor in accordance with another embodiment of the invention.

FIG. 12 illustrates an apparatus (anchor assembly or anchor 400) for anchoring a therapy catheter in accordance with another embodiment of the invention. As evident in the figures and the following description, the anchor 400 may, unlike the anchors 200 and 300, permit the connection of multiple therapy catheters 102 implanted from a single burr hole. The anchor 400 is otherwise similar in many respects to the anchors 200 and 300 already described and illustrated herein and may be used in place of the anchors 200 and 300 in various applications. As a result, where the description of various components and/or aspects of the anchor 400 would be duplicative in view of the description provided herein above of the anchors 200 and 300, such description may not be repeated below.

The anchor 400 may, in some embodiments, provide modular bays that permit attachment of various anchor modules to allow customized anchor configurations. For example, the anchor 400 may be configured with one or more therapy catheter connection modules 401 incorporating connectors 422 (see FIG. 14) similar to the connectors 222 and 322 as already described herein. As a result, a single delivery catheter 104 may feed one or more, e.g., two, therapy catheters 102. The anchor 400 may include other modules, e.g., infusion pressure measurement modules 403 (described in more detail below), blanking modules, etc., that permit construction of a wide variety of anchor configurations.

Figure 13:
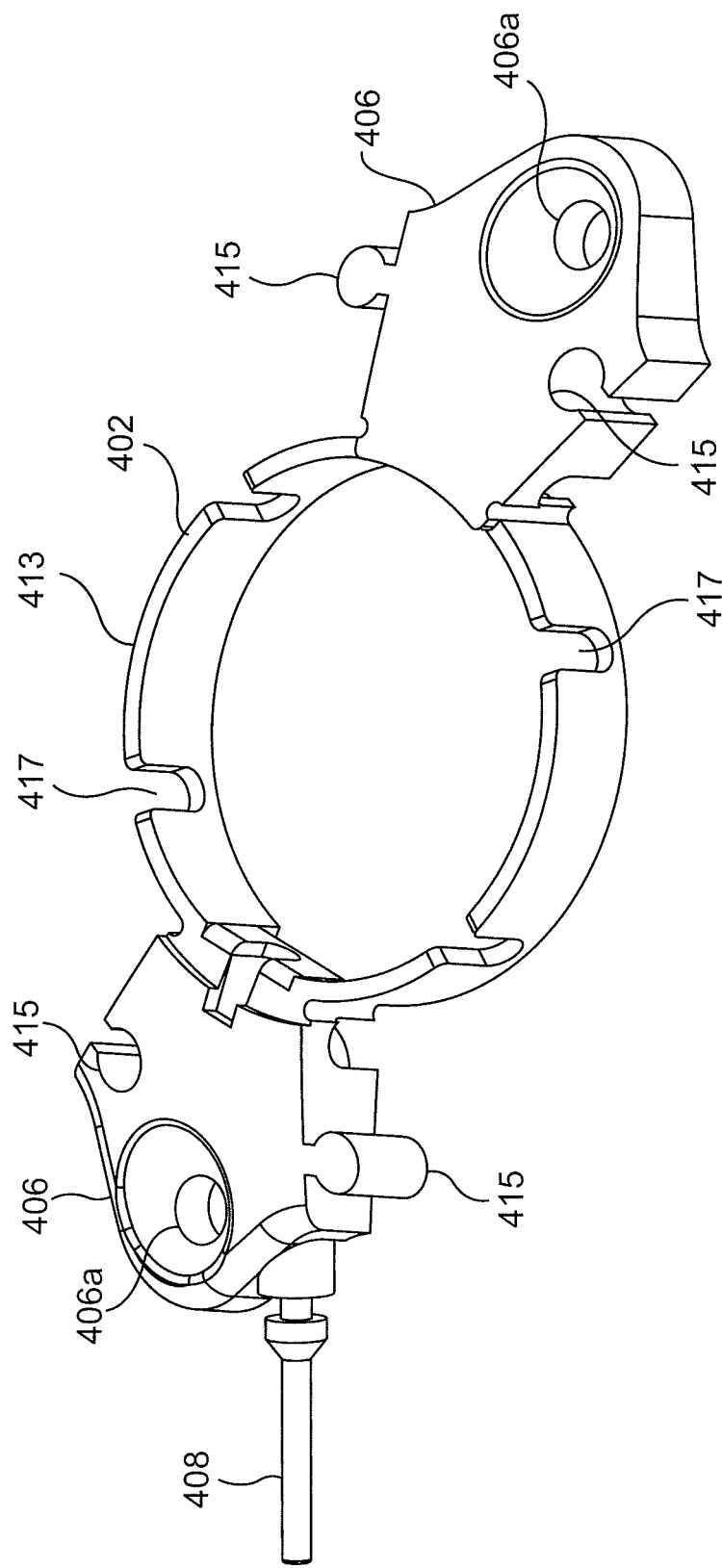
FIG. 13 is a perspective view of an exemplary base of the anchor of FIG. 12.

FIG. 13 illustrates an exemplary base 402 that may be used with the anchor 400 of FIG. 12 (the base, along with particular modules, may form an anchor body). The base 402 may form a frame or base ring 413 that surrounds a central opening through which the catheter(s) 102 may pass and further defines one or more bays each configured to receive an anchor module (e.g., module 401 or 403). The frame 412 may incorporate thereon cranial attachment members 406, e.g., bone screw openings 406a, to permit securing of the base to bone 118 (see FIG. 2) surrounding the burr hole. The members 406 may, in one embodiment, be integral with the base ring 413 as shown. Moreover, the base, e.g., one or both of the attachment members 406, may include a delivery catheter feed pin 408 (similar in many respects to the delivery catheter feed pin 208 already described herein) fixed thereto and configured to receive the feed catheter 104 (not shown). Each attachment member 406 (as well as the anchor modules discussed below) may include tabs/slots 415 that permit interlocking of the various anchor modules with one another and/or with the base 402 such that the modules 401 (e.g., connector 422) may be securely coupled to the base. The body, e.g., base ring 413, may further include slots 417 to permit, for example, routing of the various catheters from the burr hole to the desired module. The slots 417 may further form engagement surfaces, e.g., cinch points, configured to receive and immobilize the therapy catheters passing through the burr hole. In other embodiments, the cinch points may be formed by engagement surfaces on the modules.

The anchor 400 may further include an insert or cap 404 (shown separated from the anchor body in FIG. 12) that covers the opening defined by the anchor body. The cap may provide various benefits, e.g., protect the therapy catheters 102 from bodily forces and prevent tissue in-growth.

Figure 14:
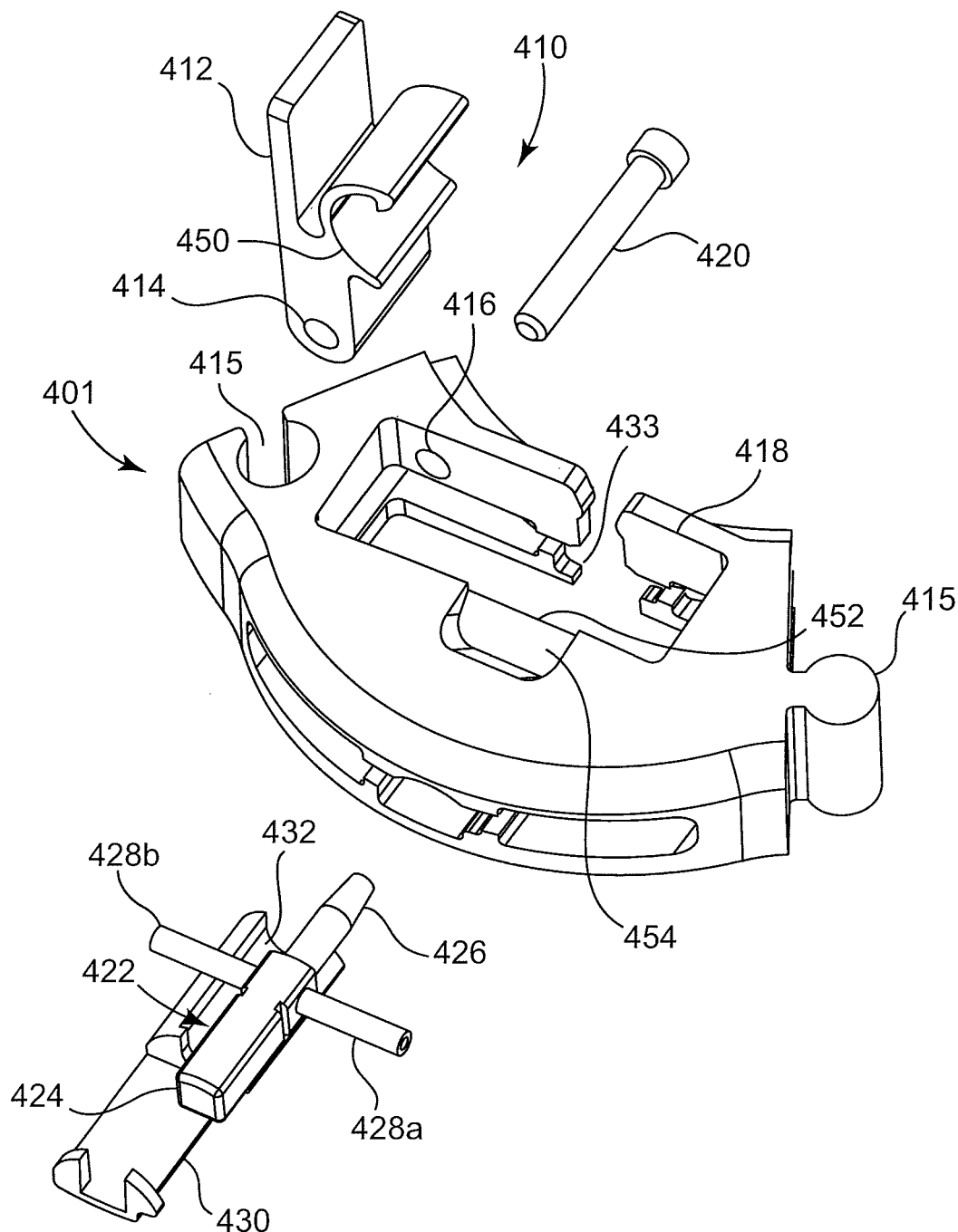
FIG. 14 is an exploded perspective view of an exemplary catheter connection module for use with the anchor of FIG. 12.

FIG. 14 illustrates an exploded perspective view of the catheter connection module 401 of FIG. 12. The illustrated module 401 may form a catheter cutting or shearing mechanism 410 similar, in many respects, to the catheter cutting mechanism 210 (see FIG. 2) described above. It may further provide a connector 422 similar in many respects to the connectors 222 and 322 already described herein.

For example, the body, e.g., module, may include an opening 433 that accommodates the connecting assembly or connector 422. It may further include a door 412 pivotally retained within a close tolerance receiving slot 418 by a pin 420 passing through a passageway 414 in the door and through a passageway 416 in the module. As a result, the mechanism, e.g., door 412, may pivot between open and closed positions to selectively shear the catheter 102.

Figure 17:
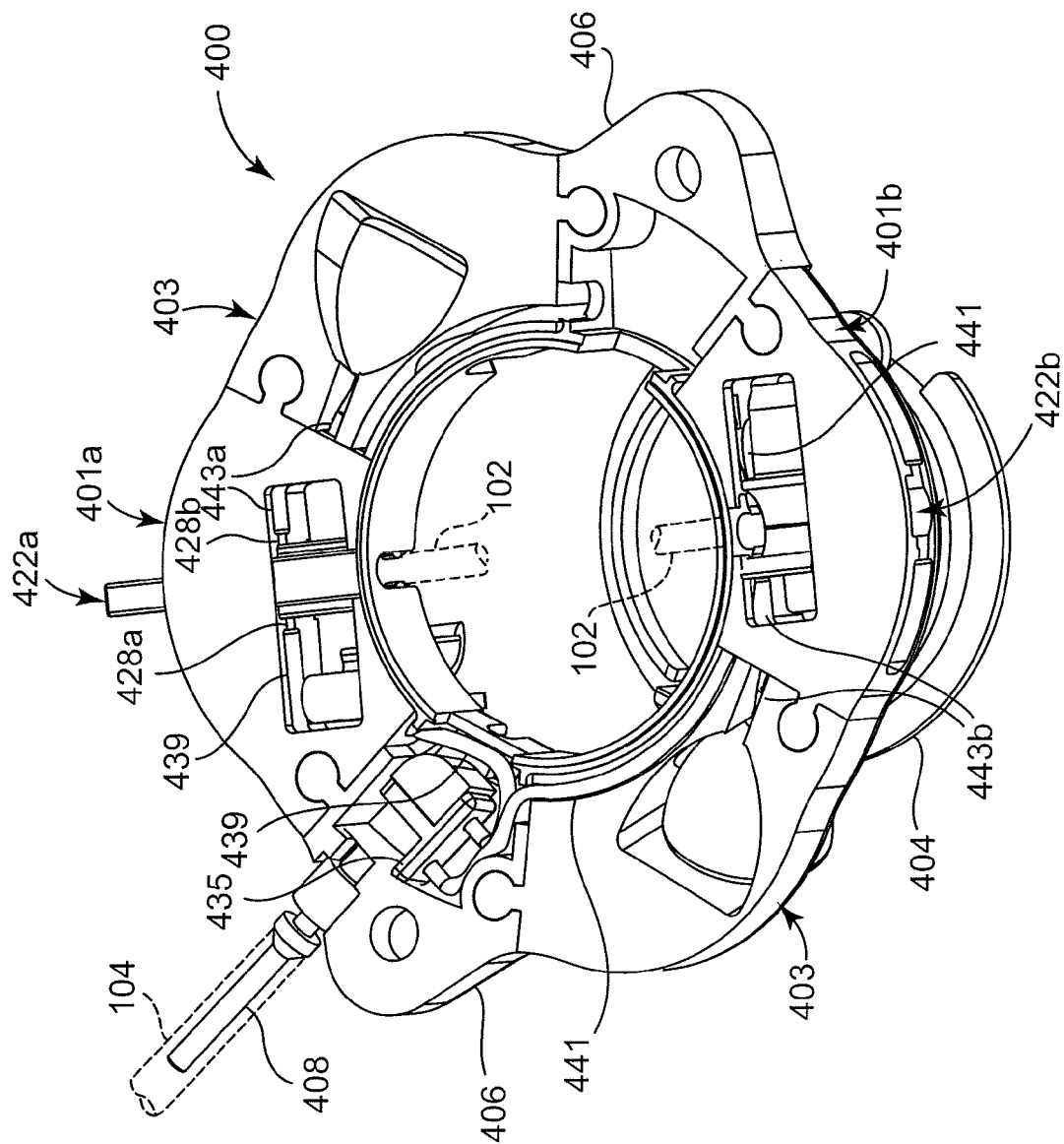
FIG. 17 is a bottom perspective view of the anchor of FIG. 12 with the cap detached.

The catheter connection module 401 may further include a guide 430 that forms a trough 432 for receiving the therapy catheter 102 (not shown). The connector 422 is movable relative to the base, e.g., translatable within the guide 430, similar to the connector 222 and guide 230 described above. The connector 422 may include a therapy catheter feed pin 426 for selective engagement with (e.g., insertion into) the therapy catheter 102 (not shown) in a manner similar to the therapy catheter feed pin 226. The connector 422 may also include at least one, e.g., two, supply pins 428 (e.g., 428a and 428b as shown in FIGS. 14 and 17; collectively referred to as pins "428"). Like the supply pin 228, one of the supply pins 428 (e.g., pin 428a) may be used to couple the connector 422 with the delivery catheter feed pin 408 (see FIG. 12) as further described below. The second supply pin 428b may be provided to permit connection to other anchor components, e.g., to the pressure measurement module 403 (see FIG. 12), as also described in more detail below. The connector may further include an actuator 424.

The connector 422 may be inserted into the opening 433 (e.g., from the inner side of the catheter connection module 401) until it abuts corresponding surfaces located within the opening near the peripheral or outer edge of the module. Once attached to the base ring 413 (see FIG. 13), the connector 422 may be secured within the module as shown in FIG. 12. The base ring 413, to which the modules described herein may also be attached, may further retain the pin 420 (see FIG. 14) in place.

As with the cutting mechanism 210 described above, the door 412 and slot 418 may define close tolerance first and second shearing edges 450 (defined by the door) and 452 (defined by an edge of the slot) and a depression 454 and relief (not shown) to assist with catheter shearing as shown in FIG. 14. Moreover, the module body and the door may be made from hardened materials similar to those already described above with reference to the door 212 and slot 218.

Once again, while described as incorporating a connector that is similar to the connector 222 already described herein, other embodiments may utilize connecting assemblies or connectors of other configurations (e.g., similar to the connector 322 also described elsewhere herein).

Figure 15:
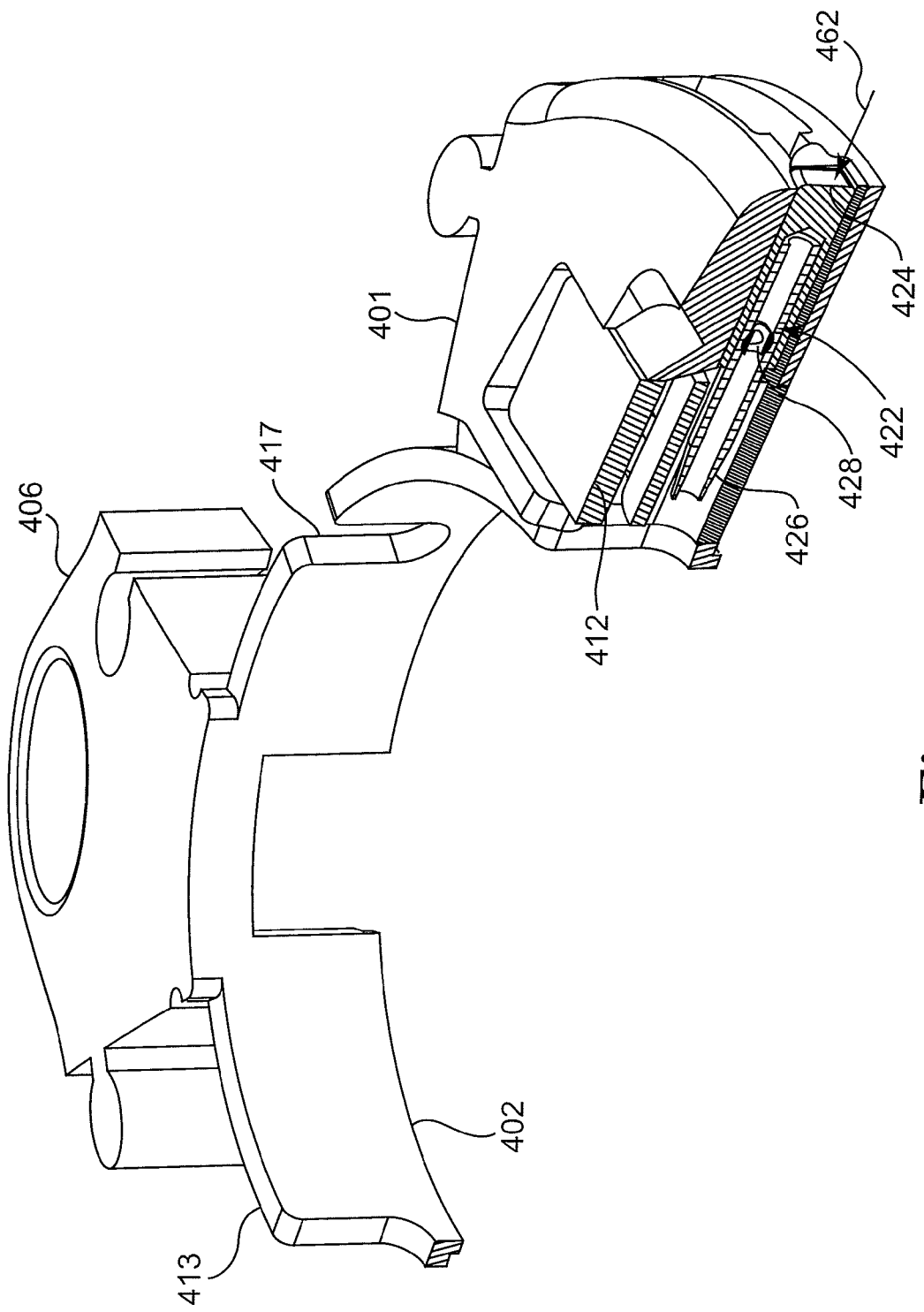
FIG. 15 is a partial perspective section view of the assembled catheter connection module of FIG. 14 as it may be attached to the base of FIG. 13.

FIG. 15 illustrates a perspective section view of a portion of the base ring 413 with the module 401 attached. As illustrated in this view, the connector 422 (and thus the therapy feed pin 426 and supply pins 428) may move in a generally radial direction 462. In particular, the connector 422 may move between a first disengaged or uncoupled position (e.g., disconnected from the therapy catheter 102), and a second engaged or coupled position (the location of the latter illustrated in FIG. 15 but with the catheter 102 removed for clarity) as these positions are already described herein (see, e.g., the connector 222 and 322).

Figure 16:
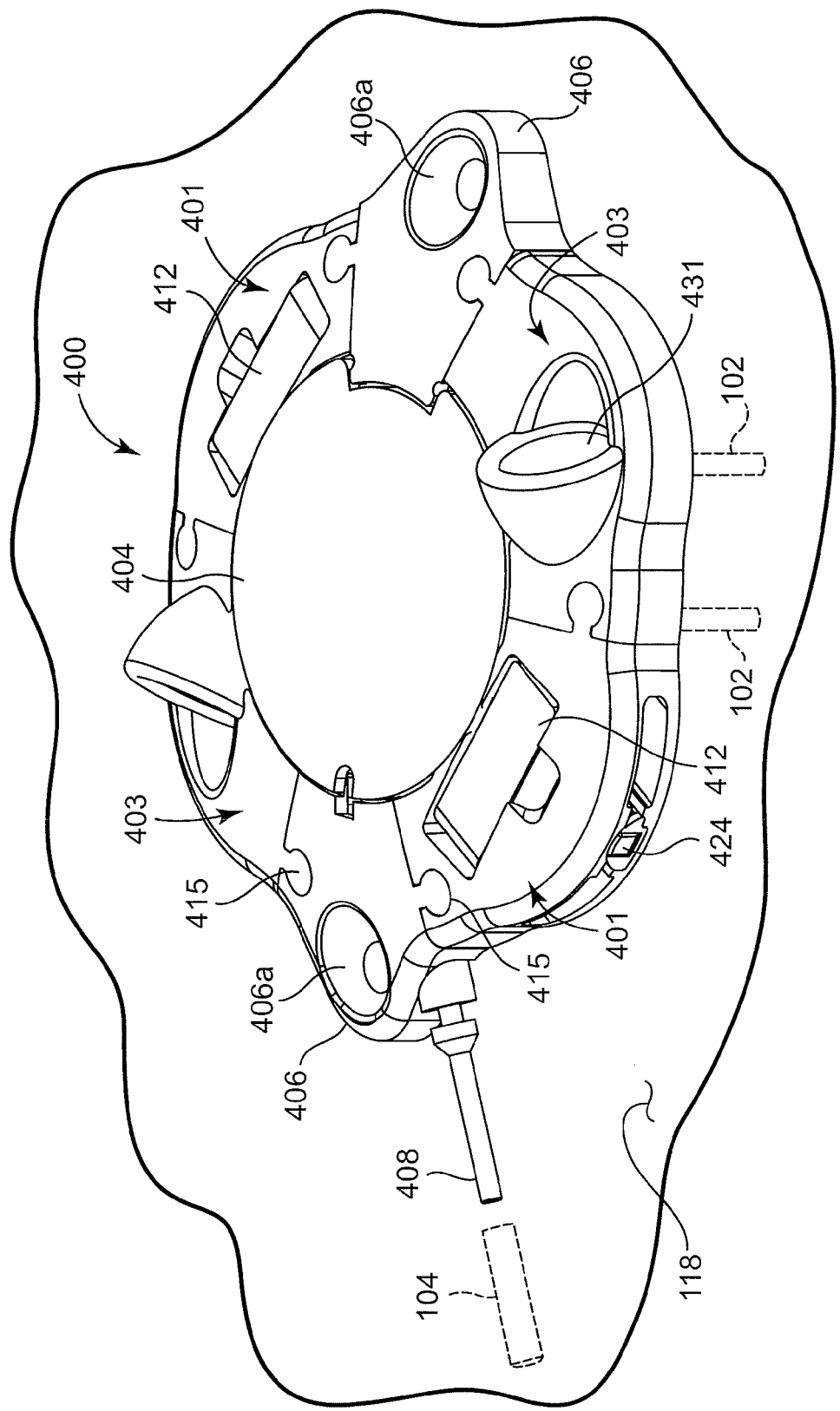
FIG. 16 is a top perspective view of the anchor of FIG. 12 as assembled and with a cap attached.

FIG. 16 illustrates the anchor 400 as assembled and attached to a cranial surface, e.g., skull bone 118, as it may be during implantation. The cap 404 is also shown attached in this view. In this particular embodiment, the single delivery catheter 104 may couple to the delivery catheter feed pin 408 where it may then feed one or more, e.g., two, therapy catheters 102. Each therapy catheter 102 may be connected, via separate catheter connection modules 401, to the delivery catheter 104, e.g., via conduits as further described below. This view further illustrates the interconnection of the various modules 401, 403 with adjacent modules and the base (e.g., attachment members 406). Moreover, this view illustrates the connectors 422 (e.g., actuators 424) in their second positions, i.e., pushed inwardly such that the therapy catheter feed pin 426 (not shown) of each fluidly couples to the proximal end of its respective therapy catheter 102.

FIG. 16 further illustrates the pressure measurement module 403 as it may be attached to the anchor. Each pressure measurement module 403 may, in one embodiment, include a needle-penetrable septum 431. The interior side of each septum may form a small reservoir that is fluidly coupled to the second supply pin 428b as further described below. As a result, the pressure of the therapeutic agent within the associated therapy catheter 102 may be verified by a clinician during or after the implantation process.

FIG. 17 is a bottom perspective view of the anchor 400 of FIG. 12. In this view, the cap 404 is shown separated from the body of the anchor, and one of the connectors 422a is shown in the first uncoupled position while the other connector 422b is shown in the second position. As shown in this view, a manifold 435 may be attached to an internal end of the delivery catheter feed pin 408. The manifold 435 may provide two separate connections to feed both of the catheter connection modules 401a and 401b. For example, a conduit, e.g., tube 439 may extend from one manifold port to the supply pin 428a of the connection module 401a, while a second tube 441 extends from a second manifold port to the supply pin (not shown) of the connection module 401b. The anchor may further include one or more supply conduits or tubes, e.g., tubes 443a and 443b, which fluidly couple the second supply pins 428b to their respective pressure measurement modules 403. Because the supply pins 428 of each connector 422 are fluidly coupled to one another as well as to their associated feed pins (not shown), the pressure within the septum-covered reservoir of the pressure measurement modules is reflective of the actual pressure in the corresponding therapy catheter 102. As a result, a clinician may insert a hypodermic needle (e.g., through the skin after implantation) through the septum and into the reservoir to measure the pressure therein in a known manner. Measuring the infusion pressure may be a valuable diagnostic tool. In some embodiments, the pressure measurement module could be used in conjunction with sensors and systems as described in U.S. Published Pat. App. No. 2008/0097287 A1 entitled SYSTEM AND METHOD FOR INTRAPARENCHYMAL DRUG INFUSION. Upon withdrawal of the needle, the septum is preferably self-sealing, e.g., made of silicone or the like. The septum may include a bacterial filter to reduce or prevent contamination of the fluid path by needle insertion through the skin.

The manifold 435 may contain flow restrictors that aid in balancing flow to each therapy catheter 102. For instance, in one embodiment, flow restrictors may be located in each path or branch of the manifold 435. These restrictors may be elements (e.g., ruby orifices) that provide the desired flow restriction (e.g., a resistance that is much greater than potential tissue resistance). In other embodiments, restrictors could be placed elsewhere in the system. For instance, a distal end of the feed catheter 104 (that attaches to the pump 106 in FIG. 1) may include a filtered connector that incorporates multiple, e.g., fused silica, lumens each having a capillary restriction to generate a desired resistance. In yet another embodiment, the implanted end of the therapy catheter 102 may include exit hole restrictors (e.g., separate internal capillaries that each have a separate exit from the therapy catheter). Any of these exemplary restrictor embodiments may also include a filter, e.g., sintered Titanium, to prevent particle clogging of the restrictive elements.

Figure 18:
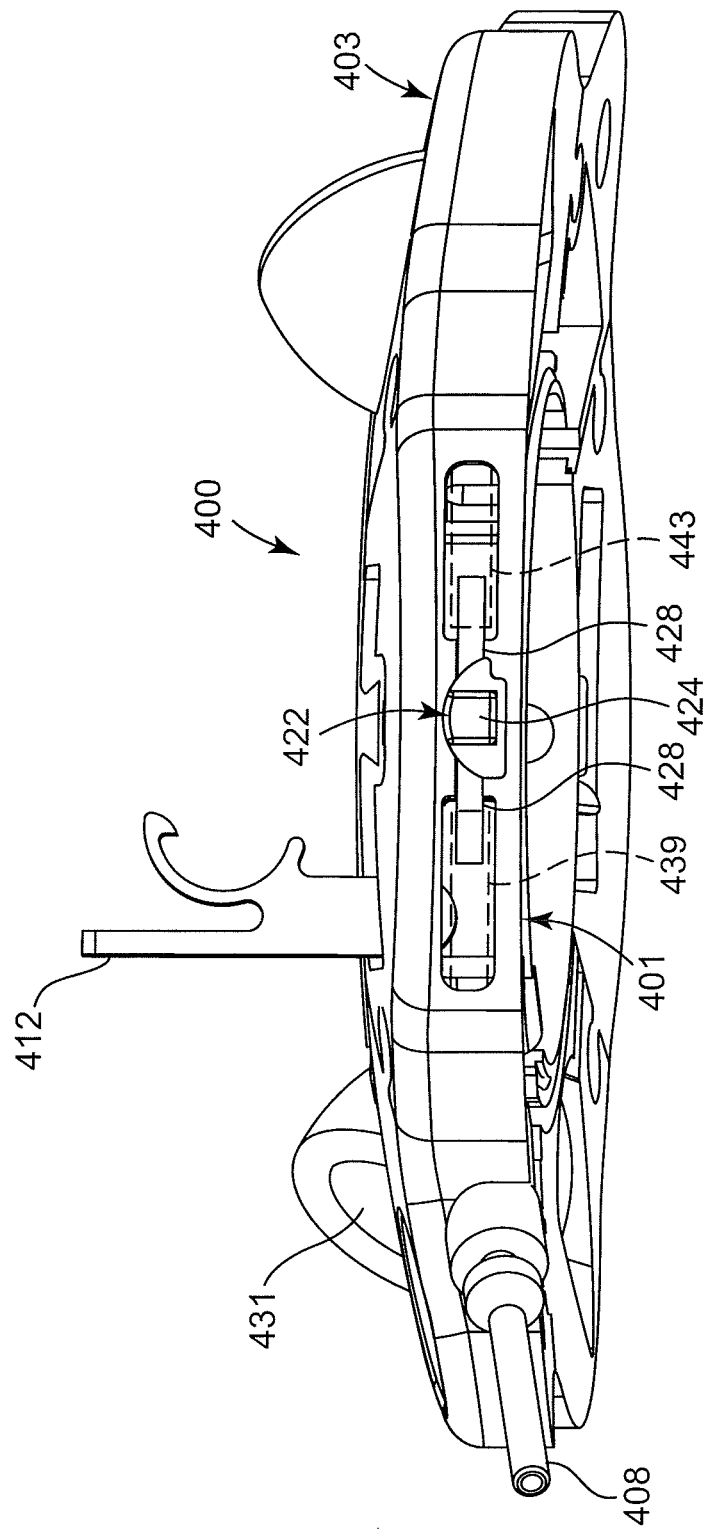
FIG. 18 is a side elevation view of the anchor of FIG. 12 with a shearing mechanism, e.g., door, shown in the open position and the cap removed.

FIG. 18 illustrates a side elevation view of the anchor 400 along an axis that is generally along one of the connectors 422. The supply pins 428, as well as their associated tubes or supply conduits 439 and 443, are visible herein. As further shown in this view, the anchor 400 may be configured to have a contoured lower surface that mimics the localized shape of the skull, e.g., it may have a slight concave shape, e.g. about a five inch radius.

Figure 19:
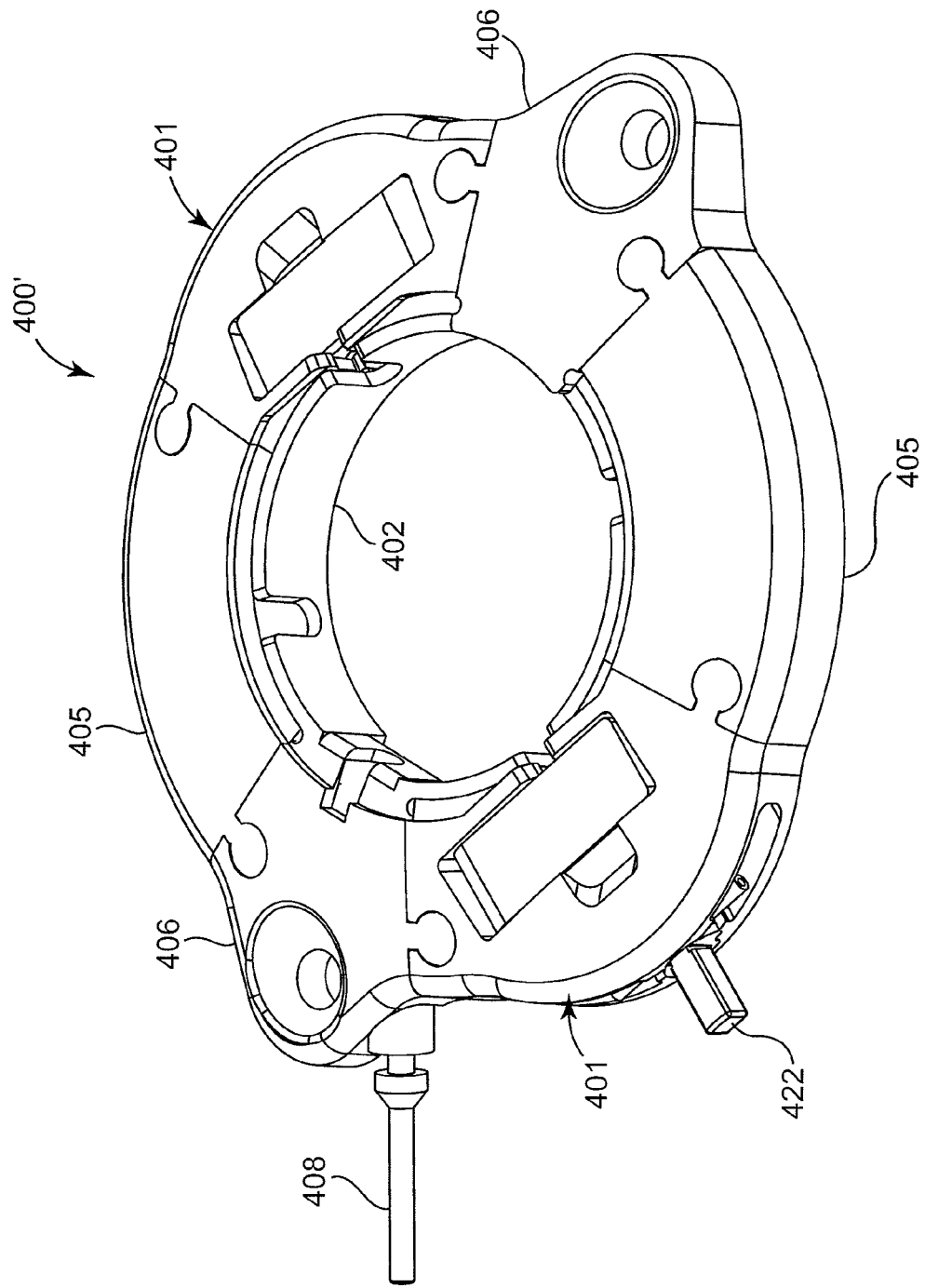
FIG. 19 is a top perspective view of an alternative embodiment of the anchor of FIG. 12.

FIG. 19 illustrates a variation of the anchor 400 indentified as anchor 400'. Like the anchor 400, the anchor 400' may include the base 402 having the attachment members 406 and one or more, e.g., two, catheter connection modules 401. However, the anchor 400' replaces the pressure measurement modules 403 of FIG. 12 with blanking plates or modules 405. The blanking modules 405 may be utilized where the pressure measuring function is unneeded. As a result, the anchor 400 (or 400') may include at least one anchor module securable within each of the provided bays, wherein the anchor module may be selected from, for example, a blanking module, a catheter connection module, and a pressure measurement module. The anchor 400' is otherwise substantially identical to the anchor 400 already described and illustrated herein.

Figure 20:
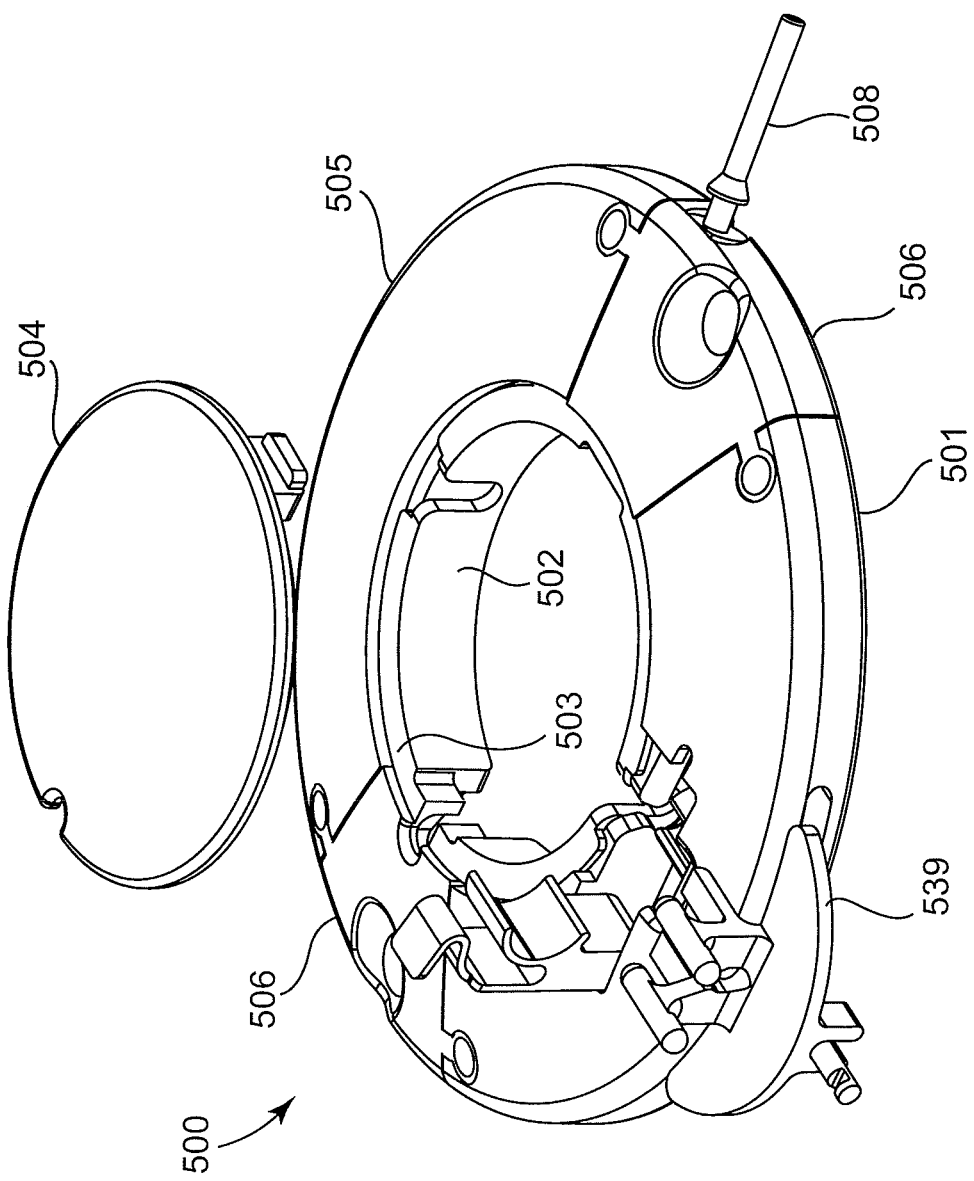
FIG. 20 is a perspective view of a burr hole anchor in accordance with yet another embodiment of the invention.
Figure 21:
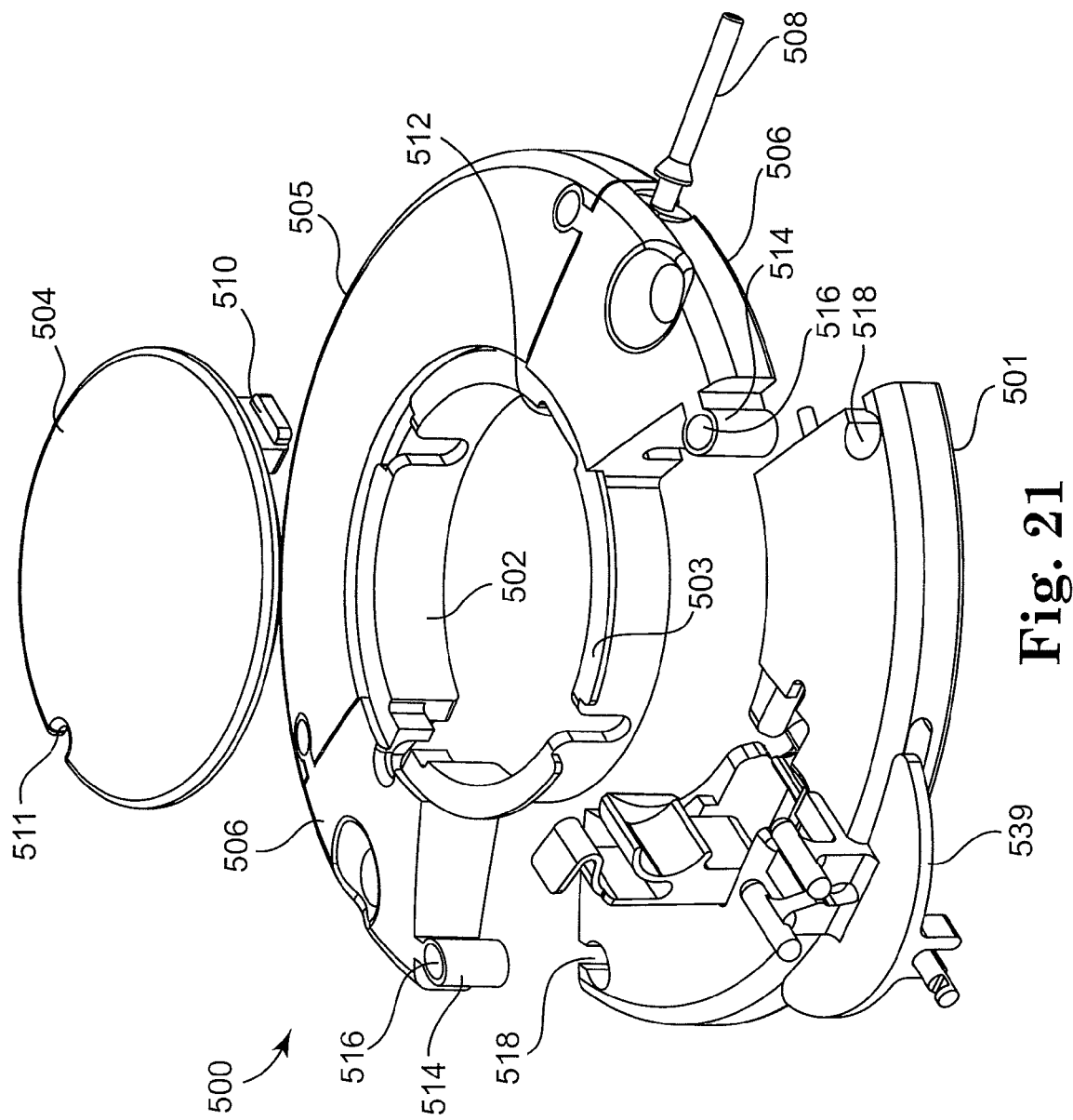
FIG. 21 is a partial exploded perspective view of the anchor of FIG. 20.

FIGS. 20-21 illustrate an apparatus (anchor 500) in accordance with another embodiment of the invention. Like the anchor 400, the anchor 500 may form a body having a base 502 with attachment members 506, and defining one or more bays that each may receive one or more modules (e.g., a catheter connection module 501 and a blanking module 505), and, optionally, a cap 504. Further, at least one of the attachment members 506 may include a delivery catheter feed pin 508 (similar in many respects to the delivery catheter feed pin 208 already described herein) configured to receive the delivery catheter 104 (not shown). In at least this embodiment, the attachment members 506 are integral to the base 502 (e.g., welded). However, in other embodiments, the attachment members could be formed separately and subsequently attached to the base.

Unless identified herein, the anchor 500 may be similar in various respects to the anchors 200, 300, and 400 already described and illustrated herein. Thus, the anchor 500 may be used in place of the anchors 200, 300, and 400 in various applications. Where the description of various components and/or aspects of the anchor 500 would be duplicative in view of the description already provided herein with respect to the other anchors, such description is not repeated below.

Unlike the anchor 400, the catheter connection module of the anchor 500 may include a clip 539 and may include cutting/connection features similar to the anchor 300 described herein with references to FIGS. 7-11B.

The cap 504 may include a retention tab 510 and a release opening 511 (see FIG. 21). The retention tab 510 may engage a retention slot 512 defined in the body (e.g., the base 502) to secure the cap 504 to the base 502. The cap 504 may be removed by inserting a tool (e.g., forceps) into the release opening 511 to remove (e.g., by prying) the cap 504 from the base 502.

During assembly of the anchor 500, a module (e.g., the catheter connection module 501) may be attached or coupled to the base 502 by matching tabs 514 of the attachment members 506 with slots 518 of the, e.g., catheter connection module 501, and sliding the catheter connection module 501 upwardly from underneath the base 502 until a portion of the top surface of the module 501 engages a flange 503 of the base 502. The flange 503 restricts the upward movement of the module 501.

Once the module 501 is secured to the base 502, a tool (e.g., conical punch) may be inserted into apertures 516 defined within the tabs 514 to enlarge or otherwise deform the tabs 514 to better secure them within the slots 518. As other aspects of the anchor 500 and modules (e.g., connection module) may have already been described herein (see, e.g., description of anchors 200, 300, and 400), no further description is provided herein.

The anchors 200 and 300 described and illustrated herein are configured primarily for applications using a single catheter per burr hole. As a result, these embodiments may be used with a relatively small burr hole (e.g., 2 mm diameter). Such anchors may find use in various applications, e.g., primate and human use. However, while described herein primarily with application to small burr holes, those of skill in the art will realize that such anchor embodiments could be scaled up (or down) for larger (or smaller) burr hole applications. The modular design of the anchors 400 and 500, on the other hand, may be configured primarily for larger, e.g., human, burr hole applications (e.g., 14 mm diameter) and may further accommodate multiple catheters (e.g., 4) per burr hole. Like the single catheter embodiments, however, modular anchors in accordance with embodiments of the present invention may also be scalable.

The systems, apparatus, and methods described herein may utilize various therapy catheters, e.g., catheters as described in U.S. patent application Ser. No. 12/276,794 entitled INFUSION CATHETER ASSEMBLY WITH REDUCED BACKFLOW. One such exemplary therapy catheter is identified as catheter assembly 600 depicted in section in FIG. 22. The catheter assembly may be used in place of the therapy catheter 102 in all embodiments described herein.

The therapy catheter assembly 600 may include a flexible and shearable tubular catheter body 606 having an inner surface and an outer surface, wherein the inner surface defines a lumen 618 extending between the catheter body's proximal and distal ends. A tubular insert, e.g., annular guide member or tube 608, may be fixed or otherwise secured relative to the catheter body (e.g., fixed to the inner surface of the lumen 618 of the body 606) near the body's distal end such that a proximal end of the guide tube is intermediate the proximal and distal ends of the catheter body. In one embodiment, the guide tube is bonded, e.g., reflow bonded, to the catheter body.

Figure 22:
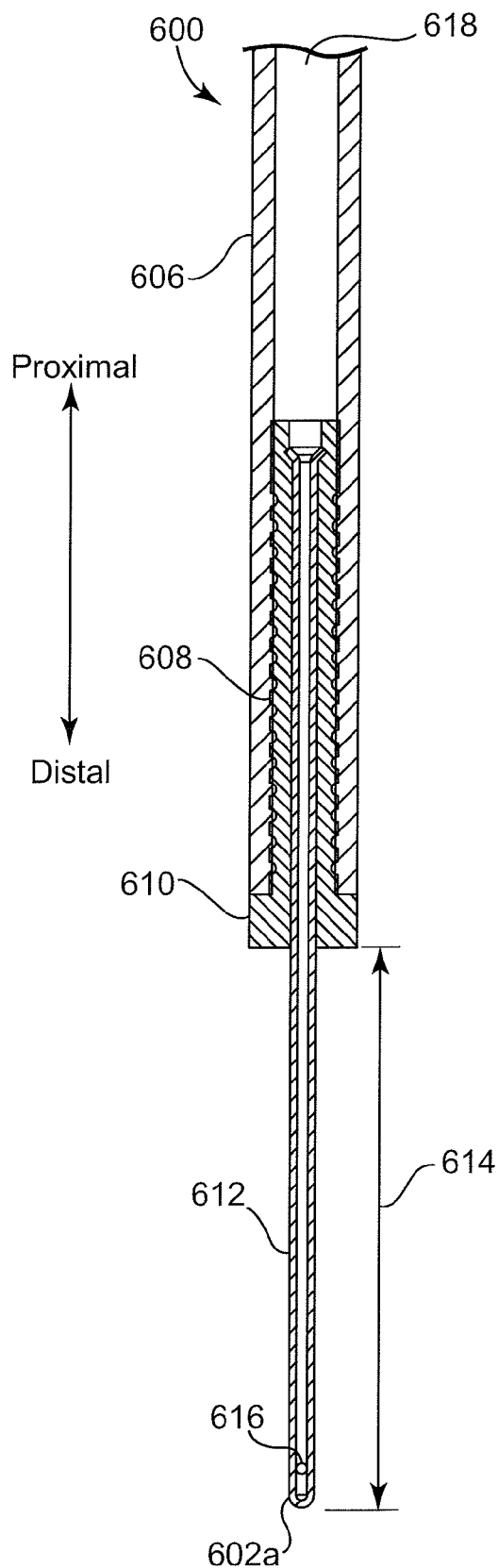
FIG. 22 is a section view of a therapy catheter in accordance with one embodiment of the invention that may be utilized with the exemplary systems, apparatus, and methods described herein.

As further shown in FIG. 22, the guide tube 608 may include a distal end having a flange or flange portion 610 that extends beyond the distal end of the catheter body 606 and may abut the same when the guide tube is fully inserted in the body.

In addition to the flange portion, the guide tube 608 may also form a sleeve or sleeve portion having an inner surface and an outer surface. The outer surface may be smooth or, alternatively, define one or more grooves (e.g., circumferential grooves) as shown in FIG. 22. Such configurations may facilitate securing of the guide tube 608 to the catheter body 606, e.g., by forming mechanical capture points or recesses into which inwardly extending portions of the body may extend.

The inner surface of the guide tube 608 may be defined by a bore extending through the guide tube. In one embodiment, the bore may be a stepped bore forming a recessed land at the proximal end of the guide tube.

A nonporous, rigid, hollow tubular needle 612 may be partially located within the lumen of the catheter body 606 and operatively fixed relative to the catheter body, e.g., fixed to an inner surface of the guide tube 608. The needle 612 may extend or protrude outwardly from the distal end of the guide tube such that a sealed distal tip 602a of the needle is located a preset distance 614 beyond the distal end of the catheter body/guide tube flange 610 as illustrated in FIG. 22.

The needle 612 may include one or more side flow openings or apertures 616 formed along an outer surface of the needle and proximate to, but offset from, the sealed distal tip. The aperture(s) 616 may be in fluid communication with the lumen 618 of the body 606 such that therapeutic substance flowing through the lumen may pass into the needle 612 (e.g., the lumen of the needle) and out through the aperture(s) 616. The needle may also include a flanged proximal end that, in one embodiment, abuts the recessed land formed in the guide tube.

The configuration of the catheter 600 may provide various benefits. For instance, the needle may provide a relatively rigid distal catheter end to aid in implantation, yet provide a flexible and shearable proximal catheter end that can be cut with the shearing mechanisms of the anchors described and illustrated herein.

While not wishing to be bound to any particular embodiment, the catheter body 606 may be constructed of 80 Shore A durometer urethane and have an inner diameter of about 0.024 in and an outer diameter of about 0.041 in. The guide tube 608 may be made from a substantially more rigid material such as polyetheretherketone (PEEK) and have a length of about 0.2 in to about 0.5 in. The needle 612 may, in one embodiment, be made of a platinum-iridium alloy. The delivery catheter 104 may form a uniform tubular member also constructed of 80 Shore A durometer urethane and have an inner diameter of about 0.024 in and an outer diameter of about 0.089 in. However, as those of skill in the art will appreciate, the materials and dimensions identified for these two catheters are exemplary only and other materials and sizes are certainly possible without departing from the scope of the invention.

Anchors, methods, and systems in accordance with embodiments of the present invention may incorporate features that permit the anchor itself to cut or trim the therapy catheter to the desired length during implantation. In other embodiments, exemplary anchors may incorporate actuatable interconnections that permit selective fluid coupling of the therapy catheter with a delivery catheter coupled to a feed port of the anchor. In still other embodiments, anchors may incorporate modular components that permit additional functionality, e.g., pressure measurement, connections for multiple therapy catheters, etc. Still further, anchors and systems in accordance with embodiments of the present invention may permit substantial isolation of the therapy catheter from bodily forces that may act outside of the burr hole, e.g., forces acting upon the delivery catheter. Moreover, apparatus in accordance with embodiments of the present invention may furthermore substantially reduce or prevent movement of the therapy catheter tip both during trimming of the therapy catheter and during subsequent connection of the therapy catheter with the delivery catheter, e.g., during engagement of the therapy catheter feed pin with the therapy catheter.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations, combinations, and modifications will be apparent to those skilled in the art without departing from the scope of the invention, and it should be understood that this invention is not limited to the illustrative embodiments set forth herein. Rather, the invention is limited only by the claims provided below, and equivalents thereof.

What is claimed is:

1. A burr hole anchor for anchoring a therapy delivery device, the anchor comprising:
    a body including a base operable to secure to bone surrounding a burr hole, wherein the body comprises engagement surfaces configured to receive and immobilize a therapy catheter passing through the burr hole;
    a connector operatively coupled to the base and movable relative thereto between at least: a coupled position, wherein the connector is fluidly connected to the therapy catheter, and an uncoupled position, wherein the connector is disconnected from the therapy catheter; and
    a catheter shearing mechanism attached to the body.

2. The anchor of claim 1, wherein the body further comprises a guide fixed relative to the base and proximate the engagement surfaces, wherein the guide comprises a trough configured to receive and support the connector for translation therein.

3. The anchor of claim 1, wherein the connector is movable in a radial direction relative to the base.

4. The anchor of claim 1, wherein the connector comprises:
    a therapy catheter feed pin configured to engage the therapy catheter when the connector is in the coupled position;
    a supply pin operatively coupled to an infusion pump, the supply pin in fluid communication with the therapy catheter feed pin; and
    an actuator for moving the connector from the uncoupled position to the coupled position.

5. The anchor of claim 4, wherein the body further comprises:
    a delivery catheter feed pin; and
    a supply conduit fluidly connecting the delivery catheter feed pin with the supply pin.

6. The anchor of claim 5, wherein the delivery catheter feed pin is fixed to the base.

7. The anchor of claim 1, wherein the base comprises a frame defining one or more bays, each bay configured to receive an anchor module.

8. The anchor of claim 7, wherein the anchor module comprises a module selected from the group consisting of a blanking module, a catheter connection module, and a pressure measurement module.

9. The anchor of claim 7, wherein the connector is attached directly to the anchor module.

10. The anchor of claim 1, wherein the connector is attached directly to the base.

11. The anchor of claim 1, wherein the body defines an opening through which the therapy catheter may pass.

12. The anchor of claim 11, wherein the engagement surfaces are defined by a slot formed through a wall of the opening.

13. The anchor of claim 1, wherein the catheter shearing mechanism comprises a door operatively attached to the body and pivotable between an open position and a closed position, the door comprising a shearing edge.

14. A burr hole anchor for anchoring a therapy delivery device, the anchor comprising:
    a body including a base operable to secure to bone surrounding a burr hole, wherein the body comprises engagement surfaces configured to receive and immobilize a therapy catheter passing through the burr hole; and
    a shearing mechanism comprising a door operatively attached to the body, the door pivotable between an open position and a closed position, the shearing mechanism operable to selectively shear the therapy catheter when placed between a first shearing edge formed by the door and a second shearing edge formed by the body.

15. The anchor of claim 14, further comprising a clip removably secured to the body and operable to hold an excess portion of the therapy catheter.

16. The anchor of claim 14, wherein the base comprises a frame defining one or more bays, each bay configured to receive an anchor module.

17. The anchor of claim 14, wherein the anchor module comprises a module selected from the group consisting of a blanking module, a catheter connection module, and a pressure measurement module.

18. The anchor of claim 14, wherein the second shearing edge of the shearing mechanism is defined by an edge of a slot formed in the body for receiving the door.

19. The anchor of claim 18, wherein the body defines a depression adjacent the second shearing edge, the depression configured to receive the therapy catheter therein.

20. A burr hole anchor system comprising:
    a therapy catheter for placement through a burr hole; and
    a burr hole anchor comprising:
        a body including a base operable to secure to bone surrounding the burr hole, wherein the body comprises engagement surfaces configured to receive and immobilize the therapy catheter passing through the burr hole; and
        a catheter shearing mechanism attached to the body, wherein the catheter shearing mechanism comprising a door pivotally attached to the body and moveable between an open position and a closed position, the door comprising a first shearing edge and the body defining a second shearing edge.

21. The system of claim 20, further comprising a connector operatively coupled to the base and movable relative thereto between at least: a coupled position, wherein the connector is fluidly connected to the therapy catheter; and an uncoupled position, wherein the connector is disconnected from the therapy catheter.

22. The system of claim 21, further comprising an infusion pump and a delivery catheter, the delivery catheter comprising a first end fluidly coupled to the connector, and a second end fluidly coupled to the infusion pump.

23. A method for trimming a therapy catheter and for securing the therapy catheter relative to a burr hole, the method comprising:
    placing the therapy catheter through the burr hole;
    securing the therapy catheter relative to bone surrounding the burr hole using a burr hole anchor, the anchor comprising:
        a body including a base that is securable to the bone surrounding the burr hole, wherein the body comprises engagement surfaces configured to receive and immobilize the therapy catheter passing through the burr hole; and
        a shearing mechanism comprising a door pivotally attached to the body and pivotable between an open position and a closed position, the shearing mechanism comprising a first shearing edge and a second shearing edge;

placing the therapy catheter between the first and second shearing edges; and moving the door from the open position to the closed position, thereby shearing an excess portion of the therapy catheter.

24. The method of claim 23, further comprising securing the excess portion of the therapy catheter within a clip removably attached to the body of the anchor before shearing the excess portion.

25. The method of claim 23, further comprising moving a connector operatively coupled to the base from an uncoupled position, wherein the connector is disconnected from the therapy catheter, to a coupled position, wherein the connector is fluidly connected to the therapy catheter.

26. The method of claim 25, further comprising coupling a first end of a delivery catheter to the connector and a second end to an infusion pump.

27. The method of claim 23, wherein securing the therapy catheter comprises securing at least two therapy catheters passing through the burr hole.

\* \* \* \* \*